US005965396A

United States Patent [19]

Pan et al.

[11] Patent Number: 5,965,396

[45] Date of Patent: Oct. 12, 1999

[54] HUMAN LYMPH NODE DERIVED GTPASE

[75] Inventors: Julie Yan Pan, Newark, Del.; Mark Egerton, Alsager, United Kingdom; David Shay Silberstein, Kennett Square, Pa.

[73] Assignee: Zeneca Limited, London, United Kingdom

[21] Appl. No.: 09/006,535

[22] Filed: Jan. 13, 1998

[51] Int. Cl.$^6$ .......................... C12P 19/34; C07H 21/04; C07H 21/02; C12N 15/11

[52] U.S. Cl. ............................ 435/69.1; 435/6; 435/440; 435/455; 435/325; 435/243; 435/320.1; 536/23.1; 536/23.2; 536/23.5; 536/24.5; 536/24.32

[58] Field of Search .............................. 435/6, 69.1, 440, 435/455, 325, 243, 320.1; 536/23.1, 23.2, 23.5, 24.5

[56] References Cited

PUBLICATIONS

Linder et al., G Proteins, Scientific American, Jul. 1992, pp. 56–65.

Finlin et al., Rem Is a New Member of the Rad– and Gem/Kir Ras–related GTP–binding Protein Family Repressed by Lipopolysaccharide Stimulation, The Journal of Biological Chemistry, vol. 272, No. 35, Issue of Aug. 29, 1997, pp. 21982–21988.

Bourne et al., The GTPase superfamily: conserved structure and molecular mechanism, Nature, vol. 349, Jan. 10, 1991, pp. 117–126.

Fischer et al., Calmodulin Binds to and Inhibits GTP Binding of the Ras–like GTPase Kir/Gem, The Journal of Biological Chemistry, vol. 271, No. 41, Oct. 11, 1996, pp. 25067–25070.

Dorin et al., Kir, a novel Ras–family G–protein, induces invasive pseudohyphal growth in *Saccharomyces cervisiae*, Oncogene (1955) 11, pp. 2267–2271.

Maguire et al., Gem: An Induced, Immediate Early Protein Belonging to the Ras Family, Science, vol. 265, 8 Jul. 1994, pp. 241–244.

Reynet et al., Rad: A Member of the Ras Family Overexpressed in Muscleof Type II Diabetes Humans, Science, vol. 262, Nov. 26, 1993, pp. 1441–1444.

Moyers et al., Overexpression of Rad Inhibitis Glucose Uptake in Cultured Muscle and Fat Cells, The Journal of Biological Chemistry, vol. 271, No. 38, Sep. 20, 1996, pp. 23111–23116.

Cohen et al., Transcriptional activation of a ras–like gene (kir) by oncogenic tyrosine kinases, Proc. Natl. Acad. Sci. USA, vol. 91, Dec. 1994, pp. 12448–12452.

Zhu et al., Rad, a Novel Ras–Related GTPase, Interacts with Skeletal Muscle β–Tropomyosin, The Journal of Biological Chemistry, vol. 271, No. 2, Issue of Jan. 12, 1996, pp. 768–773.

Zhu et al., Characterization of Rad, a New Memberof Ras/GTPase Superfamily, and Its Regulation by a Unique GTPase–activating protein (GAP)–like Activity, The Journal of Biological Chemistry, vol. 270, No. 9, Issue of Mar. 3, 1995, pp. 4805–4812.

Moyers et al., Rad and Rad–related GTPase Interact with Calmodulin and Calmodulin–dependent Protein Kinase II, The Journal of Biological Chemistry, vol. 272, No. 18, Issue of May 2, 1997, pp. 11832–11839.

*Primary Examiner*—George C. Elliot
*Assistant Examiner*—Sean M. Garry
*Attorney, Agent, or Firm*—Patrick H. Higgins

[57] ABSTRACT

A novel human GTPase polypeptide intracellular molecular switch is described. A full length cDNA which encodes the signal transduction polypeptide is disclosed as well as the interior structural region and the amino acid residue sequence of the human GTPase. Methods are provided to identify compounds that modulate the biological activity of the native signal switch biomolecule and hence regulate cellular and tissue physiology.

7 Claims, 10 Drawing Sheets

FIG.1

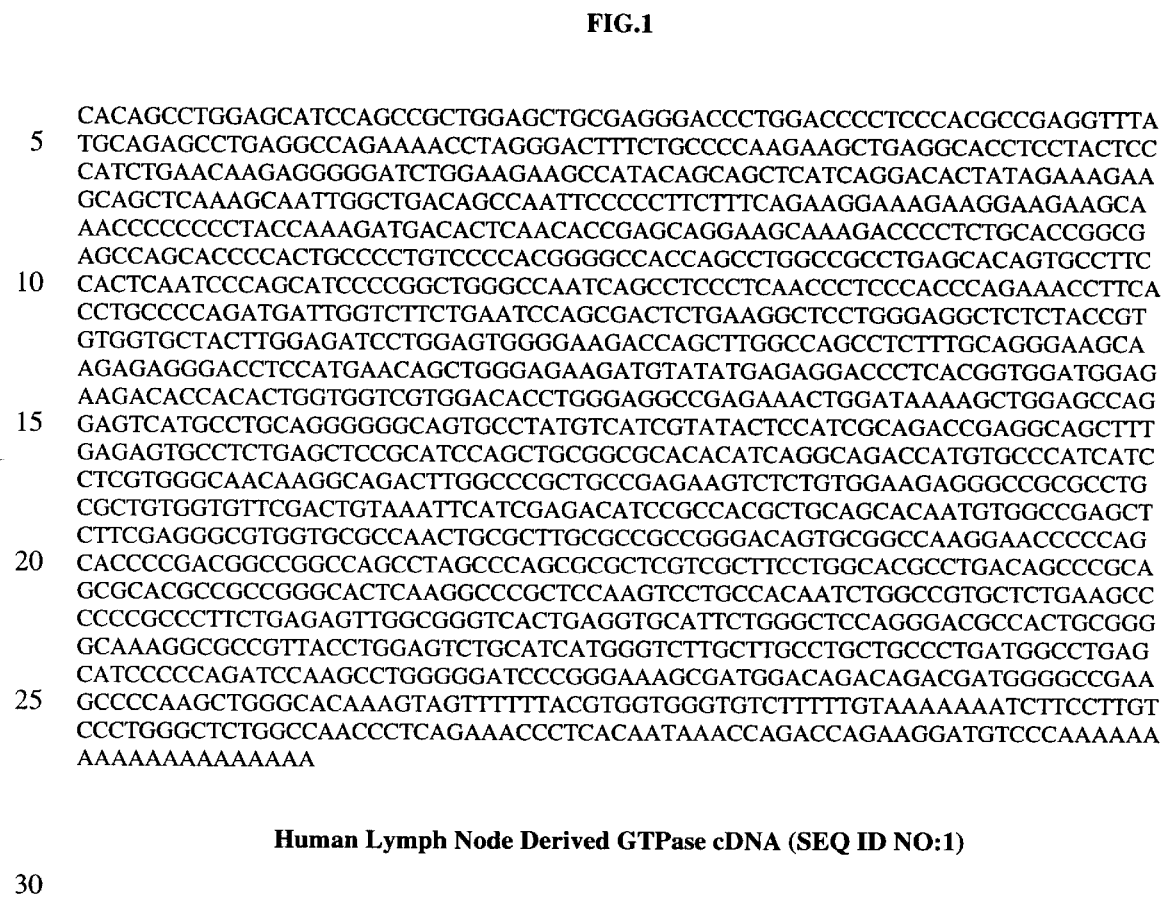

CACAGCCTGGAGCATCCAGCCGCTGGAGCTGCGAGGGACCCTGGACCCCTCCCACGCCGAGGTTTA
TGCAGAGCCTGAGGCCAGAAAACCTAGGGACTTTCTGCCCCAAGAAGCTGAGGCACCTCCTACTCC
CATCTGAACAAGAGGGGGATCTGGAAGAAGCCATACAGCAGCTCATCAGGACACTATAGAAAGAA
GCAGCTCAAAGCAATTGGCTGACAGCCAATTCCCCCTTCTTTCAGAAGGAAAGAAGGAAGAAGCA
AACCCCCCCCTACCAAAGATGACACTCAACACCGAGCAGGAAGCAAAGACCCCTCTGCACCGGCG
AGCCAGCACCCCACTGCCCCTGTCCCCACGGGGCCACCAGCCTGGCCGCCTGAGCACAGTGCCTTC
CACTCAATCCCAGCATCCCCGGCTGGGCCAATCAGCCTCCCTCAACCCTCCCACCCAGAAACCTTCA
CCTGCCCCAGATGATTGGTCTTCTGAATCCAGCGACTCTGAAGGCTCCTGGGAGGCTCTCTACCGT
GTGGTGCTACTTGGAGATCCTGGAGTGGGGAAGACCAGCTTGGCCAGCCTCTTTGCAGGGAAGCA
AGAGAGGGACCTCCATGAACAGCTGGGAGAAGATGTATATGAGAGGACCCTCACGGTGGATGGAG
AAGACACCACACTGGTGGTCGTGGACACCTGGGAGGCCGAGAAACTGGATAAAAGCTGGAGCCAG
GAGTCATGCCTGCAGGGGGGCAGTGCCTATGTCATCGTATACTCCATCGCAGACCGAGGCAGCTTT
GAGAGTGCCTCTGAGCTCCGCATCCAGCTGCGGCGCACACATCAGGCAGACCATGTGCCCATCATC
CTCGTGGGCAACAAGGCAGACTTGGCCCGCTGCCGAGAAGTCTCTGTGGAAGAGGGCCGCGCCTG
CGCTGTGGTGTTCGACTGTAAATTCATCGAGACATCCGCCACGCTGCAGCACAATGTGGCCGAGCT
CTTCGAGGGCGTGGTGCGCCAACTGCGCTTGCGCCGCCGGGACAGTGCGGCCAAGGAACCCCCAG
CACCCCGACGGCCGGCCAGCCTAGCCCAGCGCGCTCGTCGCTTCCTGGCACGCCTGACAGCCCGCA
GCGCACGCCGCCGGGCACTCAAGGCCCGCTCCAAGTCCTGCCACAATCTGGCCGTGCTCTGAAGCC
CCCCGCCCTTCTGAGAGTTGGCGGGTCACTGAGGTGCATTCTGGGCTCCAGGGACGCCACTGCGGG
GCAAAGGCGCCGTTACCTGGAGTCTGCATCATGGGTCTTGCTTGCCTGCTGCCCTGATGGCCTGAG
CATCCCCCAGATCCAAGCCTGGGGGATCCCGGGAAAGCGATGGACAGACAGACGATGGGGCCGAA
GCCCCAAGCTGGGCACAAAGTAGTTTTTTACGTGGTGGGTGTCTTTTTGTAAAAAAATCTTCCTTGT
CCCTGGGCTCTGGCCAACCCTCAGAAACCCTCACAATAAACCAGACCAGAAGGATGTCCCAAAAAA
AAAAAAAAAAAAAA

Human Lymph Node Derived GTPase cDNA (SEQ ID NO:1)

FIG.2

ATGACACTCAACACCGAGCAGGAAGCAAAGACCCCTCTGCACCGGCGAGCCAGCACCCCACTGCCC
CTGTCCCCACGGGGCCACCAGCCTGGCCGCCTGAGCACAGTGCCTTCCACTCAATCCCAGCATCCC
CGGCTGGGCCAATCAGCCTCCCTCAACCCTCCCACCCAGAAACCTTCACCTGCCCCAGATGATTGG
TCTTCTGAATCCAGCGACTCTGAAGGCTCCTGGGAGGCTCTCTACCGTGTGGTGCTACTTGGAGAT
CCTGGAGTGGGGAAGACCAGCTTGGCCAGCCTCTTTGCAGGGAAGCAAGAGAGGGACCTCCATGA
ACAGCTGGGAGAAGATGTATATGAGAGGACCCTCACGGTGGATGGAGAAGACACCACACTGGTGG
TCGTGGACACCTGGGAGGCCGAGAAACTGGATAAAAGCTGGAGCCAGGAGTCATGCCTGCAGGGG
GGCAGTGCCTATGTCATCGTATACTCCATCGCAGACCGAGGCAGCTTTGAGAGTGCCTCTGAGCTC
CGCATCCAGCTGCGGCGCACACATCAGGCAGACCATGTGCCCATCATCCTCGTGGGCAACAAGGCA
GACTTGGCCCGCTGCCGAGAAGTCTCTGTGGAAGAGGGCCGCGCCTGCGCTGTGGTGTTCGACTGT
AAATTCATCGAGACATCCGCCACGCTGCAGCACAATGTGGCCGAGCTCTTCGAGGGCGTGGTGCGC
CAACTGCGCTTGCGCCGCCGGGACAGTGCGGCCAAGGAACCCCCAGCACCCCGACGGCCGGCCAG
CCTAGCCCAGCGCGCTCGTCGCTTCCTGGCACGCCTGACAGCCCGCAGCGCACGCCGCCGGGCACT
CAAGGCCCGCTCCAAGTCCTGCCACAATCTGGCCGTGCTCTGA

Human Lymph Node Derived GTPase Structural Coding Region (SEQ ID NO:2)

FIG.3

MTLNTEQEAKTPLHRRASTPLPLSPRGHQPGRLSTVPSTQSQHPRLGQSASLNPPTQKPSPAPDDWSSES
SDSEGSWEALYRVVLLGDPGVGKTSLASLFAGKQERDLHEQLGEDVYERTLTVDGEDTTLVVVDTWE
AEKLDKSWSQESCLQGGSAYVIVYSIADRGSFESASELRIQLRRTHQADHVPIILVGNKADLARCREVSV
EEGRACAVVFDCKFIETSATLQHNVAELFEGVVRQLRLRRRDSAAKEPPAPRRPASLAQRARRFLARLT
ARSARRRALKARSKSCHNLAVL

Human Lymph Node Derived GTPase Residue Sequence (SEQ ID NO:3)

FIG.4

MTLNTQQEAKTTLRRRASTPLPLSSRGHQPGRLCTAPSAPSQHPRLGQSVSLNPPVRKPSPAQDGWSSE
SSDSEGSWEALYRVVLLGDPGVGKTSLASLFAEKQDRDPHEQLGGVYERTLSVDGEDTTLVVMDTWE
AEKLDESWCQESCLQAGSAYVIVYSIADRSSFESASELRIQLRRTHQANHVPIILVGNKADLARCREVSV
EEGRACAVVFDCKFIETSATLQHNVTELFEGVVRQLRLRRQDNAAPETPSPRRRASLGQRARRFLARLT
ARSARRRALKARSKSCHNLAVL

**REM Residue Sequence (SEQ ID NO:4). Finlin, Brian S., *et al.*, J. Biol. Chem., 272:35, 21982 (1997). The novel GTPase described herein (SEQ ID NO:3) shows 89% sequence homology to REM (SEQ ID NO:4).**

FIG.5

MTLNNVTMRQGTVGMQPQQQRWSIPADGRHLMVQKEPHQYSHRNRHSATPEDHCRRSWSSDSTDSV
ISSESGNTYYRVVLIGEQGVGKSTLANIFAGVHDSMDSDCEVLGEDTYERTLMVDGESATIILLDMWEN
KGENEWLHDHCMQVGDAYLIVYSITDRASFEKASELRIQLRRARQTEDIPIILVGNKSDLVRCREVSVSE
GRACAVVFDCKFIETSAAVQHNVKELFEGIVRQVRLRRDSKEKNERRLAYQKRKESMPRKARRFWGKI
VAKNNKNMAFKLKSKSCHDLSVL

**GEM Residue Sequence (SEQ ID NO:5). Maguire, J., *et al.*, Science, 265:241 (1994). The novel GTPase described herein (SEQ ID NO:3) shows 50% sequence homology to GEM (SEQ ID NO:5).**

FIG.6

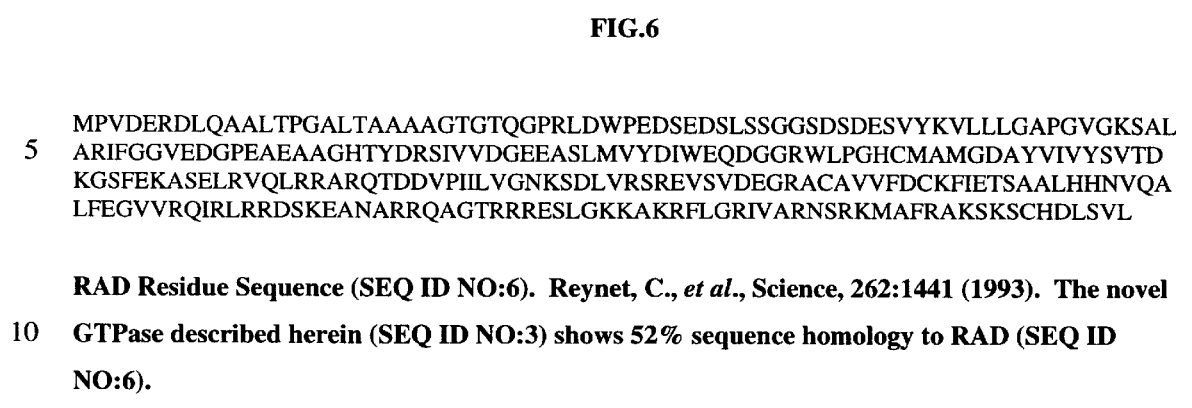

MPVDERDLQAALTPGALTAAAAGTGTQGPRLDWPEDSEDSLSSGGSDSDESVYKVLLLGAPGVGKSAL
ARIFGGVEDGPEAEAAGHTYDRSIVVDGEEASLMVYDIWEQDGGRWLPGHCMAMGDAYVIVYSVTD
KGSFEKASELRVQLRRARQTDDVPIILVGNKSDLVRSREVSVDEGRACAVVFDCKFIETSAALHHNVQA
LFEGVVRQIRLRRDSKEANARRQAGTRRRESLGKKAKRFLGRIVARNSRKMAFRAKSKSCHDLSVL

**RAD Residue Sequence (SEQ ID NO:6). Reynet, C., *et al.*, Science, 262:1441 (1993). The novel GTPase described herein (SEQ ID NO:3) shows 52% sequence homology to RAD (SEQ ID NO:6).**

Novel Human GTPase (SEQ ID NO:3) (indicated ZEN.PRO) Compared with REM (SEQ ID NO:4) (indicated MREM.PRO)

FIG.8

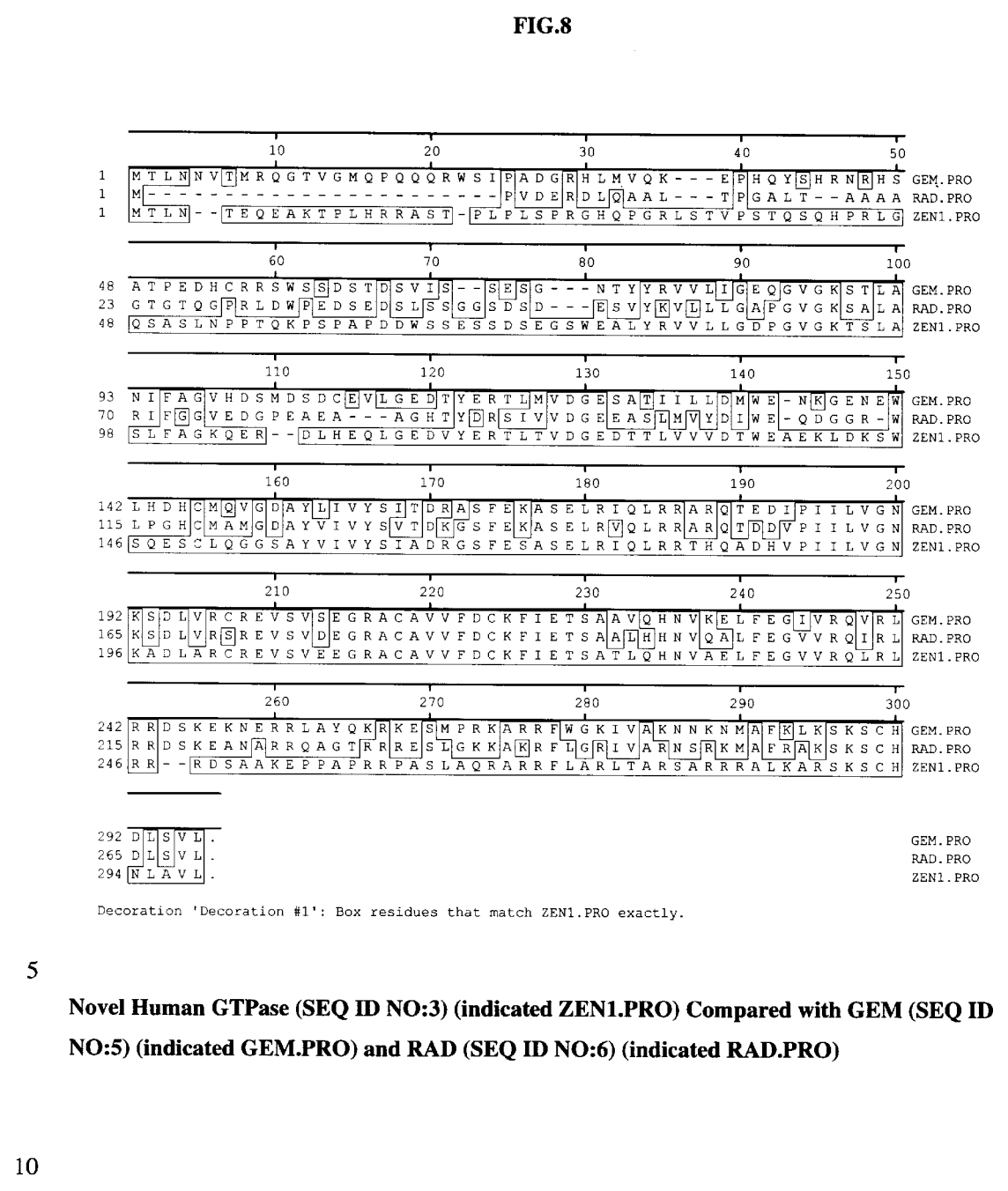

```
                       10                  20                  30                  40                  50
1   M T L N N V T M R Q G T V G M Q P Q Q Q R W S I P A D G R H L M V Q K - - - E P H Q Y S H R N R H S  GEM.PRO
1   M - - - - - - - - - - - - - - - - - - - - - - - P V D E R D L Q A A L - - - T P G A L T - - A A A A  RAD.PRO
1   M T L N - - T E Q E A K T P L H R R A S T - P L P L S P R G H Q P G R L S T V P S T Q S Q H P R L G  ZEN1.PRO

                       60                  70                  80                  90                  100
48  A T P E D H C R R S W S S D S T D S V I S - - S E S G - - - N T Y Y R V V L I G E Q G V G K S T L A  GEM.PRO
23  G T G T Q G P R L D W P E D S E D S L S S G G S D S D - - - E S V Y K V L L L G A P G V G K S A L A  RAD.PRO
48  Q S A S L N P P T Q K P S P A P D D W S S E S S D S E G S W E A L Y R V V L L G D P G V G K T S L A  ZEN1.PRO

                       110                 120                 130                 140                 150
93  N I F A G V H D S M D S D C E V L G E D T Y E R T L M V D G E S A T I I L L D M W E - N K G E N E W  GEM.PRO
70  R I F G G V E D G P E A E A - - - A G H T Y D R S I V V D G E E A S L M V Y D I W E - Q D G G R - W  RAD.PRO
98  S L F A G K Q E R - - D L H E Q L G E D V Y E R T L T V D G E D T T L V V V D T W E A E K L D K S W  ZEN1.PRO

                       160                 170                 180                 190                 200
142 L H D H C M Q V G D A Y L I V Y S I T D R A S F E K A S E L R I Q L R R A R Q T E D I P I I L V G N  GEM.PRO
115 L P G H C M A M G D A Y V I V Y S V T D K G S F E K A S E L R V Q L R R A R Q T D D V P I I L V G N  RAD.PRO
146 S Q E S C L Q G G S A Y V I V Y S I A D R G S F E S A S E L R I Q L R R T H Q A D H V P I I L V G N  ZEN1.PRO

                       210                 220                 230                 240                 250
192 K S D L V R C R E V S V S E G R A C A V V F D C K F I E T S A A V Q H N V K E L F E G I V R Q V R L  GEM.PRO
165 K S D L V R S R E V S V D E G R A C A V V F D C K F I E T S A A L H H N V Q A L F E G V V R Q I R L  RAD.PRO
196 K A D L A R C R E V S V E E G R A C A V V F D C K F I E T S A T L Q H N V A E L F E G V V R Q L R L  ZEN1.PRO

                       260                 270                 280                 290                 300
242 R R D S K E K N E R R L A Y Q K R K E S M P R K A R R F W G K I V A K N N K N M A F K L K S K S C H  GEM.PRO
215 R R D S K E A N A R R Q A G T R R R E S L G K K A K R F L G R I V A R N S R K M A F R A K S K S C H  RAD.PRO
246 R R - - R D S A A K E P P A P R R P A S L A Q R A R R F L A R L T A R S A R R R A L K A R S K S C H  ZEN1.PRO

292 D L S V L .                                                                                          GEM.PRO
265 D L S V L .                                                                                          RAD.PRO
294 N L A V L .                                                                                          ZEN1.PRO
```

Decoration 'Decoration #1': Box residues that match ZEN1.PRO exactly.

Novel Human GTPase (SEQ ID NO:3) (indicated ZEN1.PRO) Compared with GEM (SEQ ID NO:5) (indicated GEM.PRO) and RAD (SEQ ID NO:6) (indicated RAD.PRO)

FIG.9

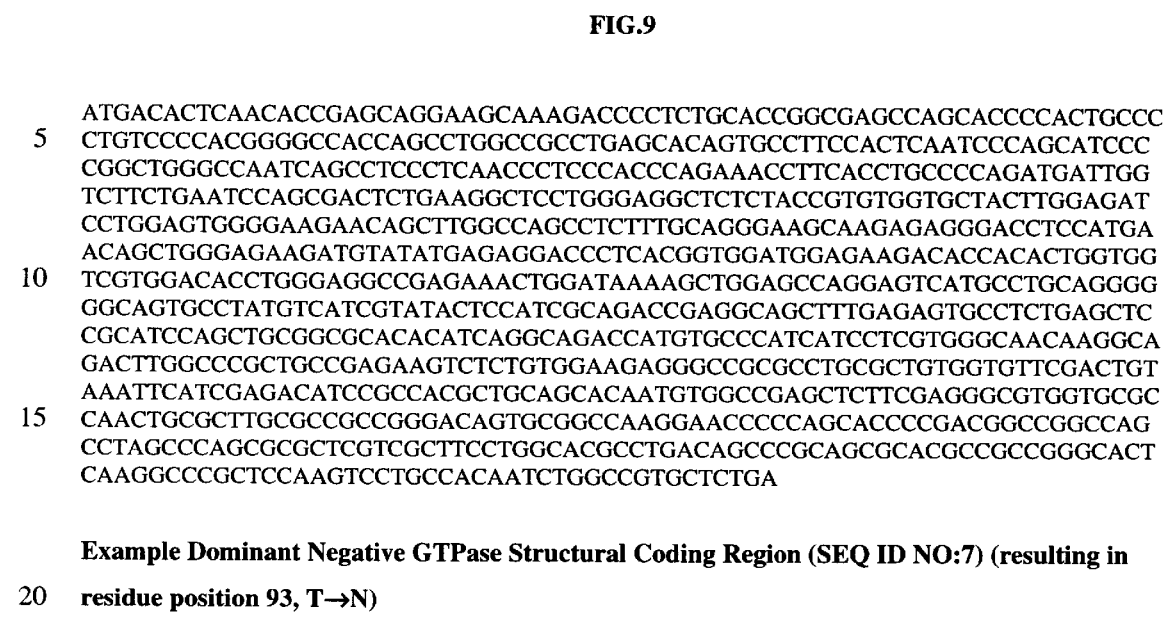

ATGACACTCAACACCGAGCAGGAAGCAAAGACCCCTCTGCACCGGCGAGCCAGCACCCCACTGCCC
CTGTCCCCACGGGGCCACCAGCCTGGCCGCCTGAGCACAGTGCCTTCCACTCAATCCCAGCATCCC
CGGCTGGGCCAATCAGCCTCCCTCAACCCTCCCACCCAGAAACCTTCACCTGCCCCAGATGATTGG
TCTTCTGAATCCAGCGACTCTGAAGGCTCCTGGGAGGCTCTCTACCGTGTGGTGCTACTTGGAGAT
CCTGGAGTGGGGAAGAACAGCTTGGCCAGCCTCTTTGCAGGGAAGCAAGAGAGGGACCTCCATGA
ACAGCTGGGAGAAGATGTATATGAGAGGACCCTCACGGTGGATGGAGAAGACACCACACTGGTGG
TCGTGGACACCTGGGAGGCCGAGAAACTGGATAAAAGCTGGAGCCAGGAGTCATGCCTGCAGGGG
GGCAGTGCCTATGTCATCGTATACTCCATCGCAGACCGAGGCAGCTTTGAGAGTGCCTCTGAGCTC
CGCATCCAGCTGCGGCGCACACATCAGGCAGACCATGTGCCCATCATCCTCGTGGGCAACAAGGCA
GACTTGGCCCGCTGCCGAGAAGTCTCTGTGGAAGAGGGCCGCGCCTGCGCTGTGGTGTTCGACTGT
AAATTCATCGAGACATCCGCCACGCTGCAGCACAATGTGGCCGAGCTCTTCGAGGGCGTGGTGCGC
CAACTGCGCTTGCGCCGCCGGGACAGTGCGGCCAAGGAACCCCCAGCACCCCGACGGCCGGCCAG
CCTAGCCCAGCGCGCTCGTCGCTTCCTGGCACGCCTGACAGCCCGCAGCGCACGCCGCCGGGCACT
CAAGGCCCGCTCCAAGTCCTGCCACAATCTGGCCGTGCTCTGA

Example Dominant Negative GTPase Structural Coding Region (SEQ ID NO:7) (resulting in residue position 93, T→N)

FIG.10

| **relative expression levels** | **tissues** | **cells** |
|---|---|---|
| high | uterus<br>lung<br>lymph node<br>kidney<br>fetal lung<br>aorta<br>heart<br>ovary | coronary artery endothelial cells<br>smooth muscle |
| moderate | mammary gland<br>small intestine<br>prostate<br>fetal heart<br>adrenal gland<br>bladder<br>thyroid<br>trachea<br>fetal spleen<br>spleen | |
| low | stomach<br>salivary gland<br>appendix<br>spinal cord<br>fetal thymus<br>pituitary gland<br>colon<br>fetal kidney<br>testes<br>liver<br>putamen<br>caudate nucleus<br>sibstantia nigra<br>skeletal muscle<br>temporal lobe<br>placenta<br>thymus<br>sub-thalamic nucleus<br>bone marrow | |
| little or none | whole brain<br>occipital lobe<br>fetal brain<br>amygdala<br>pancreas<br>cerebellum<br>fetal liver<br>cerebral cortex<br>frontal lobe<br>peripheral leukocyte<br>hippocampus<br>medulla oblongata<br>thalamus | lymphocytes (prepared from peripheral blood, including some other leukocytes, with/without stimulation by phytohemagglutinin and phorbol myristate acetate)<br>HL-60, promyelocytic leukemia<br>HeLa Cell<br>K-562, Chronic myelogenous leukemia<br>Molt-4, lymphoblastic leukemia<br>Raji - Burkitt's lymphoma<br>SW-480, colorectal adenocarcinoma<br>A549, lung carcinoma<br>G361, melanoma |

Expression Pattern of Novel GTPase in Human Tissues and Cells Detected by Northern Blot

HUMAN LYMPH NODE DERIVED GTPASE

FIELD OF THE INVENTION

The present invention relates to nucleic acid and amino acid sequences of a novel human GTPase and to the use of these sequences to identify compounds that modulate the biological activity of the native biomolecule. The invention is also related to the diagnosis, study, prevention, and treatment of pathophysiological disorders related to the biological molecule.

BACKGROUND OF THE INVENTION

G proteins function as cellular biological switches, which effectively determine when and for how long signal transduction pathways are activated. The biological switch is activated when GTP (guanosine triphosphate) is bound, and inactivated when GTP is hydrolyzed to GDP (guanosine diphosphate). The rate of hydrolysis determines the duration between biological activation of the signal pathway and deactivation. G protein signal transducers form a superfamily of GTPases. GTPase family members, most notably the products of ras genes, regulate the rate of cell division. Linder, M. E., et al., Scientific American, 56:56 (1992).

Many important cell-surface receptors for hormones and sensory stimuli, for example, transduce extracellular stimuli into cellular responses by promoting formation of the GTP-bound state of their GTPase targets. Each protein in the family is a precisely engineered molecular switch that can change its affinities for other macromolecules. Turned on by binding GTP and off by hydrolysing GTP to GDP, the switch mechanism is remarkably versatile, enabling different GTPases to sort and amplify transmembrane signals, direct the synthesis and translocation of proteins, guide vesicular traffic through the cytoplasm, and control proliferation and differentiation of cells. As targets of mutation and microbial toxins, GTPases have pivotal roles in the pathogenesis of cancer and infectious diseases. Bourne, H. R., et al., Nature, 349:117 (1991).

Ras is a small guanine nucleotide binding GTPase that transduces biological information from the cell surface to the nucleus. Its ability to transfer growth signals from receptor tyrosine kinases to a mitogen activated protein kinase (MAPK) cascade puts it in the heart of signaling pathways that cause proliferation in normal cells and uncontrolled growth in cancer cells. Indeed, mutations that lock Ras in its active, GTP-bound state lead to malignant transformation and are among the most frequently identified mutations in human cancers. Barbacid, M., Annu. Rev. Biochem., 56:779 (1987); McCormick, F., Nature, 363:15–16 (1993). The Ras family of low molecular weight GTP-binding proteins has been implicated in a wide range of cellular processes, including cell growth and differentiation, intracellular vesicular trafficking, nucleocytoplasmic transport, and cytoskeletonal reorganization. Bourne, H. R., et al., Nature, 348:125 (1990); Zerial, M., et al., *Guidebook to the Small GTPases*, Oxford University Press, New York (1995).

A newly described subfamily of Ras-like GTPases composed of the Rad, Kir, and Gem proteins is now apparent. Finlin, B. S., et al., J. Biol. Chem., 272:35, 21982 (1997). The members of this Ras subfamily are subject to transcriptional regulation. Rad is overexpressed in muscle of type II diabetes patients and Kir/Gem expression is induced by oncogenic kinases (reviewed infra). Kahn, C. R., et al., Science, 262:1441 (1993); Cohen, L. et al., *Transcriptional Activation of a Ras-like Gene (Kir) by Oncogenic Tyrosine*

*Kinases*, PNAS, 91:12448 (1994). Non-insulin dependent diabetes mellitus (NIDDM, or Type II diabetes) is among the most common metabolic disorders, affecting up to 6% of the population of the United States. The high incidence of diabetes in certain populations and among first-degree relatives of Type II diabetic patients, as well as the high concordance in identical twins, provide strong evidence that genetic factors underlie susceptibility to this disease. Reynet, C., et al., Rad: A Member of the Ras Family Overexpressed in Muscle of Type II Diabetic Humans, Science, 262:1441 (1993). Rad has also been shown to associate with skeletal muscle β-tropomyosin and the cytoskeleton of muscle cells and to inhibit insulin-stimulated glucose uptake in a variety of cultured cell lines. Zhu, J., et al., *J. Biol. Chem.* 271:2, 768 (1996); Moyers, J. S., et al., J. Biol. Chem., 271:23111 (1996).

The mRNA levels of both Kir and Gem are transcriptionally induced in activated T-lymphocytes. lymphocytes. Finlin, B. S., et al., J. Biol. Chem., 272:35, 21982 (1997). Murine Kir and Gem nucleotide sequences are 98.4% identical in their coding sequence and most likely encode the same protein or very highly related proteins, referred to as Kir/Gem. Cohen, L. et al., *Transcriptional Activation of a Ras-like Gene* (*Kir*) by Oncogenic Tyrosine Kinases, PNAS, 91:12448 (1994). Gem, shares significant sequence homology with Rad and is a mitogen-induced immediate early gene product in T lymphocytes. Zhu, J., et al., J. Biol. Chem., 271:2, 768 (1996). Moreover, deregulated expression of Gem has been demonstrated to prevent proliferation of normal and transformed 3T3 cells, clearly suggesting that Gem is involved in regulating signaling pathways that influence cell growth. Maguire, J., et al., Science. 265:241 (1994). Furthermore, cellular levels of Kir are dramatically increased in pre-B cells transformed by a set of abl tyrosine kinase oncogenes. Cohen, L. et al., PNAS, 91:12448 (1994). The correlation between Kir expression and the tumorigenic and metastatic potential of BCL/ABL and v-ABL transformed cells suggests that Kir participates in the processes of metastasis. Genetic analysis moreover suggests that Kir acts upstream of the STE20 kinase and results in the activation of a mitogen-activated protein kinase (MAPK) cascasde. Doreen, D. et al., Oncogene, 11:2267 (1995). These results are consistent with an increasingly accepted model in which members of the Kir/Gem and Rad subfamily, regulate growth-related cellular signaling cascades by controlling the activity of mitogen-activated protein kinases (MAPK). Finlin, B. S., et al., J. Biol. Chem., 272:35, 21982 (1997); Fischer, R., et al., J. Biol. Chem., 271:41, 25067 (1996).

Evidence has demonstrated that MAPK and stress activated protein kinase (SAPK) signal transduction pathways are responsible for triggering biological effects across a wide variety of pathophysiological conditions including conditions manifested by dysfunctional leukocytes, T-lymphocytes, acute and chronic inflammatory disease, auto-immune disorders, rheumatoid arthritis, osteoarthritis, transplant rejection, macrophage regulation, endothelial cell regulation, angiogenesis, atherosclerosis, fibroblasts regulation, pathological fibrosis, asthma, allergic response, ARDS, atheroma, osteoarthritis, heart failure, cancer, diabetes, obeisity, cachexia, Alzheimers disease, sepsis, and neurodegeneration. As MAP kinases play a central role in signaling events which mediate cellular responses, controlling the activity of MAPK is key to the attenuation of the response. N. J. Holbrook, et al., *Stress-Inducible Cellular Responses*, 273, Feige, U., et al., Eds., Birkhauser Verlag (1996).

Angiogenic response of vascular endothelium, endothelial cell proliferation, is one of the first steps in angiogenesis. VEGF, bFGF, and EGF all upregulate MAP kinase in HUVEC cells. The establishment and remodeling of blood vessels is controlled by paracrine signals, many of which are protein ligands that bind and modulate the activity of transmembrane receptor tyrosine kinases (RTKs). The basic view of RTK signaling has come from studies (performed largely in fibroblasts) of ligand-dependent autophosphorylation and activation of the branched Ras pathways. Results suggest that most RTKs are similarly coupled into the intracellular signal transduction cascade and are capable of inudcing endothelial cell proliferation. Hanahan, D., *Signaling Vascular Morphogenesis and Maintenance, =l Science,* 227:48 (1997).

Finlin et al. recently reported the cDNA cloning and characterization of a murine GTP-binding protein, Rem (for Rad and Gem-related). Alignment of the full-length open reading frame of mouse Rem revealed the encoded protein to be 47% identical to the Rad, Gem, and Kir proteins. The distinct structural features of the Rad, Gem, and Kir subfamily are maintained including a series of nonconservative amino acid substitutions at positions important for GTPase activity and a unique sequence motif thought to direct membrane association. Recombinant Rem is reported to bind GTP in a specific and saturable manner. The administration of LPS (lipopolysaccharide) to mice, a potent activator of the inflammatory and immune systems, results in the general repression of Rem mRNA levels in a dose- and time-dependent manner. The unique structure of Rem, its enrichment in tissues with a large number of vascular endothelial cells, its ability to specifically bind GTP, and its regulation by LPS suggest that it may control cellular pathways in endothelial cells. Finlin, B. S., et al., J. Biol. Chem., 272:35, 21982 (1997). Finlin, B. S., et al., *Rem is a New Member of the Rad- and Gem/Kir Ras-Related GTP-Binding Protein Family Repressed by Lipopolysaccharide Stimulation*, J. Biol. Chem., 272:35, 21982 (1997). See also, regarding hypertension, Iiri, T., et al., Nature Genetics, 18:8, et seq (1998).

Compounds which are able to modulate the activity of specific signal transduction molecules integral to specific intracellular pathways are expected to have significant potential for the ability to control or attenuate downstream physiological responses. Unfortunately, in spite of the introduction of numerous new drugs during the last three decades, there is a need for new, more efficient and less toxic compounds. Accordingly, the ability to identify such compounds is of paramount importance.

Rem is an exemplary biological candidate of the newly described subfamily of Ras-like GTPases for angiogenesis regulation as well as regulation of functional physiology in endothelial and smooth muscle cells, rates of cell division, differentiation, as well as peripheral vascular disease, inflammation, arteriosclerosis, hypertension, pathogenesis of cancer and infectious diseases, COPD (chronic obstructive pulmonary disease), leukocyte physiology, T-lymphocyte activity, diabetes, as well as cell activation, shape, and motility, inter alia. However, the previously reported Rem GTPase is a murine isolate. The availability of a functional human homolog will be ideal for such drug screening as well as diagnosis, study, prevention, and treatment of pathophysiological disorders related to the biological molecule.

SUMMARY OF THE INVENTION

The present invention is directed to an isolated and purified polynucleotide molecule, which encodes a polypeptide of a GTPase, or a biologically active derivative thereof comprising a nucleic acid sequence encoding the polypeptide having the sequence substantially as depicted in SEQ ID NO:3 or a biologically active fragment thereof. Isolated and purified polynucleotides of the present invention include but are not limited to SEQ ID NO:1 (novel human GTPase cDNA) and SEQ ID NO:2 (novel human GTPase structural coding region).

In addition, the current invention is directed to a purified polypeptide comprising the amino acid sequence substantially as depicted in SEQ ID NO:3 which functions as a human GTPase signal switch polypeptide.

The invention is further directed to an expression vector for expression of a GTPase polypeptide in a recombinant host cell, wherein said vector contains a polynucleotide comprising a nucleic acid sequence encoding a biological signal polypeptide having the sequence substantially as depicted in SEQ ID NO:3 or a biologically active derivative thereof.

Further the invention is directed to a host cell containing an expression vector for expression of a GTPase polypeptide, wherein said vector contains a polynucleotide comprising a nucleic acid sequence encoding the polypeptide of a GTPase having the sequence substantially as depicted in SEQ ID NO:3 or a biologically active derivative thereof. The invention is also directed to a method for producing a polypeptide which has the ability to bind GTP under physiological conditions having the amino acid sequence substantially as depicted in SEQ ID NO:3 by culturing said host cell under conditions suitable for the expression of said polypeptide, and recovering said polypeptide from the host cell culture.

The instant invention is further directed to a method of identifying compounds that modulate the biological activity of a GTPase, comprising:

(a) combining a candidate compound modulator of GTPase biological activity with a GTPase polypeptide having the sequence substantially as depicted in SEQ ID NO:3, and (b) measuring an effect of the candidate compound modulator on the biological activity.

The instant invention is further directed to a method of identifying compounds that modulate the biological activity of a GTPase, comprising:

(a) combining a candidate compound modulator of GTPase biological activity with a host-cell expressing a GTPase polypeptide having the sequence substantially as depicted in SEQ ID NO:3, and (b) measuring an effect of the candidate compound modulator on the biological activity.

The instant invention is further directed to a method of identifying compounds that modulate cell physiology, comprising:

(a) combining a candidate compound modulator of cell physiology with a host-cell expressing a polypeptide of a GTPase having the sequence substantially as depicted in SEQ ID NO:3, and (b) measuring an effect of the candidate compound modulator on the cell physiology.

The present invention is also directed to active compounds identified by means of the aforementioned methods, wherein said compounds modulate the biological activity of a human GTPase.

The present invention is also directed to active compounds identified by means of the aforementioned methods, wherein said compounds modulate cell physiology.

Further, the invention is directed to a pharmaceutical composition comprising a compound active in at least one of the aforementioned methods, wherein said compound is a modulator of the biological activity of a human GTPase.

Further, the invention is directed to a pharmaceutical composition comprising a compound active in at least one of the aforementioned methods, wherein said compound is a modulator of human cell physiology.

Additionally, the invention is directed to a novel treatment of a patient in need of such treatment for a condition which is mediated by GTPase, comprising administration of a GTPase modulating compound active in at least one of the aforementioned methods.

The invention is further directed to an antisense poynucleotide molecule comprising substantially the complement of SEQ ID NO:2 or a biologically-effective portion thereof as well as a method for inhibiting the expression of a GTPase biological switch molecule comprising administering an effective amount of the antisense molecule.

The invention is further directed to an antisense poynucleotide molecule comprising substantially the complement of SEQ ID NO:2 or a biologically-effective portion thereof as well as a method for modulating physiology in a cell comprising administering an effective amount of the antisense molecule.

The current invention is also drawn toward an antibody specific for a purified polypeptide comprising the amino acid sequence substantially as depicted in SEQ ID NO:3.

The invention is also directed to various diagnostic compositions for the identification of a polypeptide sequence comprising the amino acid sequence substantially as depicted in SEQ ID NO:3.

BRIEF DESCRIPTION OF THE FIGURES

FIG. 1 displays SEQ ID NO:1 which is a 1525 base cDNA nucleic acid sequence which encodes the novel human GTPase signal transduction polypeptide described herein.

FIG. 2 displays SEQ ID NO:2 which is the 897 base translated structural coding region, ATG to TGA, of the cDNA nucleic acid sequence which encodes the novel human GTPase polypeptide described herein.

FIG. 3 displays SEQ ID NO:3 which is the 298 amino acid residue sequence of the novel human GTPase polypeptide described herein.

FIG. 4 shows SEQ ID NO:4 which is the 297 amino acid residue sequence of the recently described murine REM molecule. Finlin, Brian S., et al., J. Biol. Chem., 272:35, 21982 (1997).

FIG. 5 shows SEQ ID NO:5 which is the 296 amino acid residue sequence of the GEM molecule. Maguire, J., et al., Science, 265:241 (1994).

FIG. 6 shows SEQ ID NO:6 which is the 269 amino acid residue sequence of the RAD molecule. Reynet, C., et al., Science, 262:1441 (1993).

FIG. 8 exhibits a comparison between the amino acid residue sequence of the novel human GTPase polypeptide described herein (SEQ ID NO:3) (designated ZEN 1.PRO), and the amino acid residue sequences of GEM (SEQ ID NO:5) (designated GEM.PRO), and RAD (SEQ ID NO:6) (designated RAD.PRO). Non-conserved amino acid residues are boxed. Dashes represent gaps introduced to optimize the alignment. Sequences shown in this figure were produced using the multisequence alignment program of DNASTAR software (DNASTAR Inc, Madison Wis.).

FIG. 9 displays SEQ ID NO:7 which is an example 897 base translated structural coding region, ATG to TGA, nucleic acid sequence which encodes the novel human GTPase polypeptide described herein resulting in a residue position 93, T→N Dominant Negative Mutant GTPase.

FIG. 10 shows the tissue distribution and relative expression patterns of the novel GTPase, as demonstrated via Northern blot analyses.

DETAILED DESCRIPTION OF THE INVENTION

Figure 7:
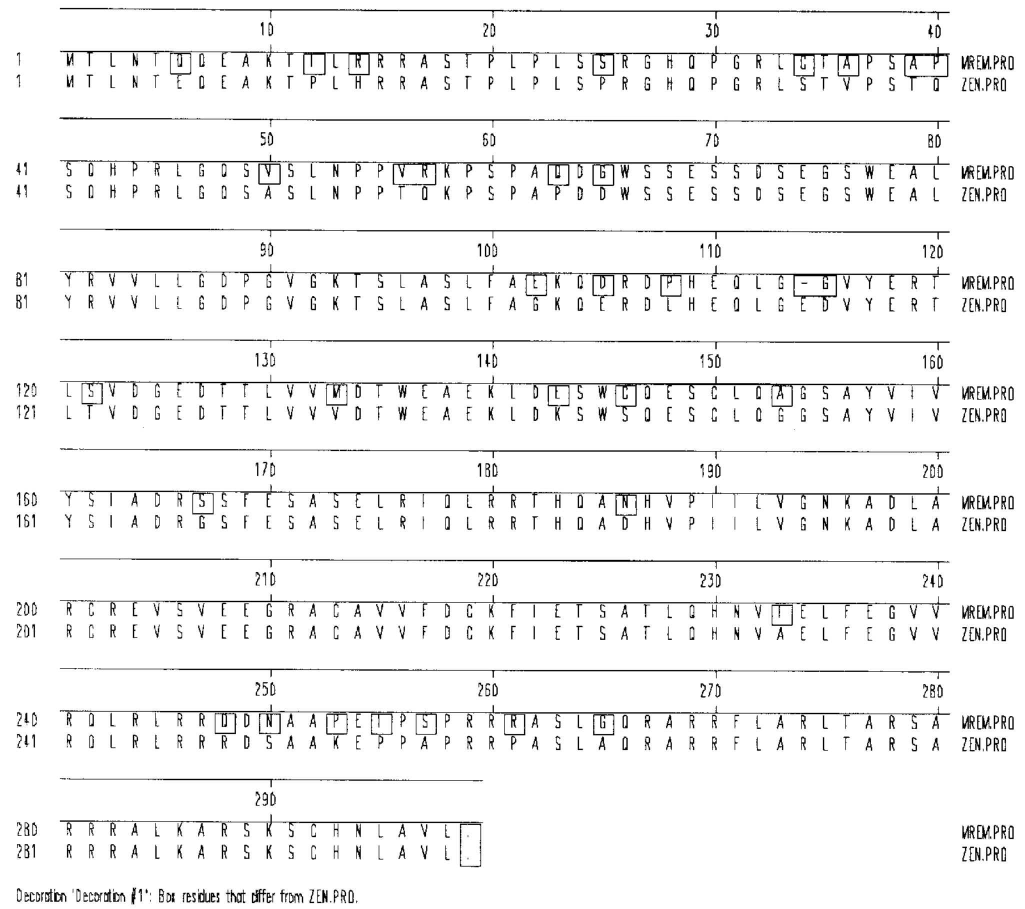
FIG. 7 exhibits a comparison between the amino acid residue sequence of the novel human GTPase polypeptide described herein (SEQ ID NO:3) (designated ZEN.PRO), and the amino acid residue sequences of REM (SEQ ID NO:4) (designated MREM.PRO). Non-conserved amino acid residues are boxed. Dashes represent gaps introduced to optimize the alignment. Sequences shown in this figure were produced using the multisequence alignment program of DNASTAR software (DNASTAR Inc, Madison Wis.).

Unless defined otherwise, all technical and scientific terms used herein have the same meaning as is commonly understood by one of skill in the art to which this invention belongs. All publications and patents referred to herein are incorporated by reference.

Nucleic acid sequence as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. Similarly, amino acid and/or residue sequence as used herein refers to peptide or protein sequences or portions thereof.

Purified as used herein refers to molecules, either nucleic acid or amino acid sequences, that are removed from their natural environment and isolated or separated from at least one other component with which they are naturally associated.

As used herein, a functional derivative of a human GTPase molecule disclosed herein is a compound that possesses a biological activity (either functional or structural) that is substantially similar to SEQ ID NO:3. The term "functional derivatives" is intended to include the "fragments," "variants," "degenerate variants," "analogs" and "homologues", and to "chemical derivatives". The term "variant" is meant to refer to a molecule substantially similar in structure and function to either an entire GTPase molecule or to a fragment thereof. A molecule is "substantially similar" to a GTPase polypeptide if both molecules have substantially similar structures or if both molecules possess similar biological activity. The term "analog" refers to a molecule substantially similar in function to either an entire native biological switch GTPase polypeptide, or to a fragment thereof.

Biological activity as used herein refers to, but is not limited to, the ability to bind GTP and/or calmodulin.

Modulate the biological activity of GTPase as used herein refers to down regulation via antagonization, repression, neutralization, or sequestration, of a biological signal switch polypeptide including but not limited to the novel human GTPase described herein; as well as up regulation or agonization thereof by a compound identified by means described herein. The term "modulation" is generally used herein to refer to the capacity to either enhance or inhibit a functional property. Such enhancement or inhibition may be contingent on the occurrence of a specific event, such as activation of a signal transduction pathway, and/or may be manifest only in particular cell types.

Modulate cell physiology as used herein refers to cell division, differentiation, leukocyte activity, manifestation of cell activation, cell shape, motility, altered cytology, and the like; as well as tissue physiology including but not limited to hypertension, inflammation, arteriosclerosis, angiogenesis, COPD (chronic obstructive pulmonary disease), diabetes, acute and chronic inflammatory disease, peripheral vascular disease, auto-immune disorders, rheumatoid arthritis, osteoarthritis, transplant rejection, macrophage regulation, endothelial cell regulation, fibroblasts regulation, pathological fibrosis, asthma, allergic response, ARDS, atheroma, heart failure, cancer, obeisity, cachexia, Alzheimers disease, sepsis, and neurodegeneration.

"Substantially as depicted" as used herein refers to functional derivative proteins, peptides and DNA sequences that may have changes but perform substantially the same biological function in substantially the same way.

Biologically active fragment as used herein includes peptides which have been truncated with respect to the N- or C-termini, or both; or the corresponding 5' or 3' end, or both, of the corresponding polynucleotide coding region, which fragments perform substantially the same biological function or encode peptides which perform substantially the same function in substantially the same way. The term "biologically active" also refers to the activity of a homolog or analog entity having structural, regulatory or biochemical functions substantially the same as the naturally occurring entity. Expression vector as used herein refers to nucleic acid vector constructions which have components to direct the expression of heterologous protein coding regions including coding regions of the present invention through accurate transcription and translation in host cells. Expression vectors usually contain a promoter to direct polymerases to transcribe the heterologous coding region, a cloning site at which to introduce the heterologous coding region, and usually polyadenylation signals. Expression vectors include but are not limited to plasmids, retroviral vectors, viral and synthetic vectors.

Transformed host cells as used herein refer to cells which have coding regions of the present invention stably integrated into their genome, or episomally present as replicating or nonreplicating entities in the form of linear nucleic acid or transcript or circular plasmid or vector.

Direct administration as used herein refers to the direct administration of nucleic acid molecules which encode reagents (e.g., GTPase, modulator compound molecule, antisense molecule, antibody molecule) of the present invention or fragments thereof; and the direct administration of reagents of thc present invention or fragments thereof, per se; and the in vivo introduction of molecules of the present invention preferably via an effective eukaryotic expression vector in a suitable pharmaceutical carrier. Polynucleotides and therapeutic molecules of the present invention may also be delivered in the form of nucleic acid transcripts.

Ras Superfamily

GTPases of the Ras superfamily contain five well conserved amino acid motifs involved in guanine nucleotide binding and hydrolysis. Boume, H. R., et al., Nature, 348:125 (1990); Valencia, A., et al., Biochemistry, 30:4637 (1991). These primary sequence motifs have been evolutionarily conserved and define a conserved structure whose importance has been confirmed through extensive mutational analysis. Bourne, H. R. et al., (1991) *Nature* 349, 117–127). The sequence of all GTPases share approximately 20–30% amino acid identity, whereas the sequence identity is considerably higher within subfamilies. Kahn, R. A., et al., FASEB J., 6:2512 (1992). Many GTPases a are modified by isoprenylation at characteristic C-terminus target sequences, such as CAAX in Ras. A new class of GTPases has recently emerged which comprise the human molecules Rad (Reynet, C., et al., Science, 262:1441 (1993)) and Gem (also known as "Kir") (Maguire, J., et al., Science, 265:241 (1994); Cohen, L., et al., Proc. Natl. Acad. Sci., 91:12448 (1994)). These molecules are neoteric in that they have a novel, common C-terminus, and their expression is inducible and/or tissue specific. A murine GTPase of this subfamily, "Rem", has also recently been described. See, Finlin, Brian S., et al., J. Biol. Chem., 272:35, 21982 (1997).

Kir/Gem

Cohen et al., reported the characterization of a member of the ras gene family, named Kir, that is overexpressed in cells transformed by abl tyrosine kinase oncogenes encodes a protein of 33 kDa. *Transcriptional Activation of a Ras-like Gene (Kir) by Oncogenic Tyrosine Kinases*, PNAS, 91:12448 (1994). [Kir for kinase-inducible ras-like, whose expression is tightly regulated by BCR/ABL and v-Abl oncogenic protein-tyrosine kinases].

Maguire et al. reported the cloning of Gem, an immediate-early gene expressed in mitogen-stimulated stimulate T cells, Kir appears to be highly related to Gem and is a close relative of the type II diabetes-associated Rad gene. Maguire, J., et al., Science. 265:241 (1994); Reynet, C., et al., Rad: A Member of the Ras Family Overexpressed in Muscle of Type II Diabetic Humans, Science, 262:1441 (1993). Kir and Gem are almost identical in their coding sequences but diverge in their 5' untranslated sequences. The cloning of two genes that encode identical or highly related proteins and are inducible by oncogenic tyrosine kinases or phobol esters suggests an important role for this subfamily of small guanine nucleotide-binding proteins in the control of cell response to growth stimuli. Murine kir and gem nucleotide sequences are 98.4% identical in their coding sequence and most likely encode the same protein or very highly related proteins, referred to as Kir/Gem. The Kir/Gem protein has an estimated molecular weight of 33,838 and is composed of 295 amino acid residues. Kir/Gem and Rad show 61% amino acid identity and 74% conservation. Gem expression has been demonstrated to prevent proliferation of normal and transformed 3T3 cells, suggesting that Gem is a regulatory protein, possibly participating in receptor-mediated signal transduction at the plasma membrane. The correlation between kir overexpression and the highly tumorigenic and metastic phenotype of the BCR/ABL-expressing pre-B cells suggests that kir may be involved in processes of invasion or metastasis. Cohen et al., PNAS, 91:12448 (1994). Moreover, calmodulin binds to and inhbits GTP binding of the ras-like GTPase Kir/Gem. Fischer, R., et al., J. Biol. Chem., 271:41, 25067 (1996).

Rad

Rad has a 61% amino acid sequence identity to Gem and Kir, respectively, whereas the latter proteins are 98% identical to each other. Reynet, C., et al., Rad: *A Member of the Ras Family Overexpressed in Muscle of Type II Diabetic Humans*, Science, 262:1441 (1993); Fischer, R., et al., J. Biol. Chem., 271:41, 25067 (1996). Rad has been shown to interact with skeletal muscle β-tropomyosin and the cytoskeleton of muscle cells in a GTP-dependent manner suggesting that Rad may be involved in skeletal muscle motor function and cytoskeletal organization. Moreover, Rad expression is increased in skeletal muscle of type II diabetes, whereas Gem and Kir are increased in activated T-lymphocytes and pre-B cells, respectively. Zhu, J., et al., *J. Biol. Chem.* 271:2, 768 (1996). That Ras-like proteins of the Kir/Gem and Rad type appear to play an important role in growth-related signaling has recently been demonstrated by the finding that Kir functions upstream of the ste30 kinase in activating mitogen-activated protein kinase (MAPK) cascades. Doreen, D. et al., Oncogene, 11:2267 (1995).

Rem

Finlin et al. recently reported the cDNA cloning and characterization of a murine GTP-binding protein, Rem (for Rad and Gem-related). The distinct structural features of the Rad, Gem, and Kir subfamily are maintained including a series of nonconservative amino acid substitutions at positions important for GTPase activity and a unique sequence motif thought to direct membrane association. The cDNA encodes a protein of 297 amino acids with a calculated molecular size of 32,893 Da. The Rem protein contains a core sequence (amino acids 84–246) that is highly related to members of the Ras superfamily of small GTP-binding proteins. The highest degree of similarity previously shown was with mouse and human Gem, Kir, and Rad (46.7–47.2% sequence identity). Recombinant Rem is reported to bind GTP in a specific and saturable manner. The administration of LPS (lipopolysaccharide) to mice, a potent activator of the inflammatory and immune systems, results in the general repression of Rem mRNA levels in a dose- and time-dependent manner. Although several previously characterized Ras-like genes including the Rad, Gem, and Kir genes are known to be regulated by transcriptional induction, Rem is the first Ras-related GTP-binding protein demonstrated to undergo suppression of MRNA levels in response to stimulation. The unique structure of Rem, its enrichment in tissues with a large number of vascular endothelial cells, its ability to specifically bind GTP, and its regulation by LPS suggest that it may control cellular pathways in endothelial cells. Finlin, B. S., et al., Rem is a New Member of the Rad- *and Gem/Kir Ras-Related GTP-Binding Protein Family Repressed by Lipopolysaccharide Stimulation*, J. Biol. Chem., 272:35, 21982 (1997).

Human Lymph Node Derived GTPase

A full length cDNA which encodes a novel human signal switch polypeptide is disclosed (SEQ ID NO: 1) as well as the interior structural coding region (SEQ ID NO:2) and the amino acid residue sequence of the human GTPase (SEQ ID NO:3). Methods are provided to identify compounds that modulate the biological activity of the native signal switch biomolecule and hence regulate cellular and tissue physiology.

FIG. 1 displays SEQ ID NO:1 which is a 1525 base cDNA nucleic acid sequence which encodes the novel human GTPase signal transduction polypeptide described herein. FIG. 2 displays SEQ ID NO:2 which is the 897 base translated structural coding region, ATG to TGA, of the cDNA nucleic acid sequence which encodes the novel human GTPase polypeptide. FIG. 3 displays SEQ ID NO:3 which is the 298 amino acid residue sequence of theGTPase. FIG. 4 shows SEQ ID NO:4 which is the 297 amino acid residue sequence of the recently described murine REM molecule. Finlin, Brian S., et al., J. Biol. Chem., 272:35, 21982 (1997). The novel GTPase described herein (SEQ ID NO:3) shows 89% sequence homology to REM (SEQ ID NO:4). FIG. 7 exhibits a comparison between the amino acid residue sequence of the novel human GTPase polypeptide described herein (SEQ ID NO:3) (designated ZEN.PRO), and the amino acid residue sequences of REM (SEQ ID NO:4) (designated MREM.PRO).

Analysis of the full-length sequence (SEQ ID NO:1) shows that it contains GTP binding domains (G1=GAPGVGK; G2=EQDG; G3=NKSD; G4=ETSA) and a calmodulin-binding domain (KRFLGRIVARNSRKMAFRAKSKS). The GTPase was expressed in *E. coli* as a fusion protein with glutathione sulfonyl transferase for in vitro experiments. The novel molecule binds GTP as well as calmodulin as demonstrated by the assays described infra. Moreover, a mutant form of the fusion protein (SEQ ID NO:7), with a T93N substitution was expressed. This molecule fails to bind GTP and is expected to act as a dominant negative mutant when expressed in heterologous cells. FIG. 9 displays SEQ ID NO:7 which is the example 897 base translated structural coding region, ATG to TGA, nucleic acid sequence which encodes the novel human GTPase polypeptide described herein resulting in a residue position 93, T→N Dominant Negative Mutant GTPase.

A human tissue expression-profile of the novel biomolecule was constructed via Northern Blot analysis as shown in FIG. 10. The novel GTPase appears to be expressed at a particularly high level in endothelial and smooth muscle cells, which is similar to the reported distribution of murine Rem in tissues with a large number of vascular endothelial cells, suggesting that it may control cellular pathways in endothelial cells. In view of the expression pattern and evidentiary characterization, the novel GTPase described herein has significant propensity as a target for the regulation of endothelial and smooth muscle cell and tissue physiological conditions including but not limited to hypertension, inflammation, arteriosclerosis, angiogenesis, and peripheral vascular disease. The novel biomolecule is an exemplary biological candidate of the newly described subfamily of Ras-like GTPases for angiogenesis regulation as well as regulation of functional physiology in endothelial and smooth muscle cells, rates of cell division and differentiation, as wel as inflammation, arteriosclerosis, hypertension, pathogenesis of cancer and infectious diseases, COPD (chronic obstructive pulmonary disease), leukocyte physiology, T-lymphocyte activity, diabetes, as well as other conditions mediated by cell activation, shape, and motility, inter alia. An important objective of pharmacological approaches now available is the control of the vascular endothelial cell barrier.

Moreover due to the fact that other members of the Ras-like subfamily, of which the novel biomolecule (SEQ ID NO:3) is a member, appear to play an important role in growth-related signaling, as recently demonstrated by the finding that Kir functions upstream of the Ste20 kinase in activating mitogen-activated protein kinase (MAPK) cascades, the novel GTPase described herein has significant potential for triggering biological effects across a wide variety of pathophysiological conditions including conditions manifested by dysfunctional leukocytes, T-lymphocytes, acute and chronic inflammatory disease, auto-immune disorders, rheumatoid arthritis, osteoarthritis, transplant rejection, macrophage regulation, endothelial cell regulation, angiogenesis, atherosclerosis, fibroblasts regulation, pathological fibrosis, asthma, allergic response, ARDS, atheroma, osteoarthritis, heart failure, cancer, diabetes, obeisity, cachexia, Alzheimers disease, sepsis, and neurodegeneration.

The availability of this functional human homolog will be ideal for such drug screening as well as diagnosis, study, prevention, and treatment of pathophysiological disorders related to the biological molecule.

Variants

The present invention also encompasses variants of the native GTPase signal switch biomolecule SEQ ID NO:3. A variant is one having at least 90% amino acid sequence similarity; and a most preferred variant is one having at least 95% amino acid sequence similarity to the human GTPase molecule amino acid sequence (SEQ ID NO:3) or a biologically active fragment thereof.

A "variant" of the GTPase molecule of the present invention may have an amino acid sequence that is different by one or more amine acid "substitutions". The variant may have "conservative" changes, wherein a substituted amine acid has similar structural or chemical properties, eg, replacement of leucine with isoleucine. More rarely, a variant may have "nonconservative" changes, eg, replacement of a glycine with a tryptophan. Similar minor variations may also include amine acid deletions or insertions, or both. Guidance in determining which and how many amine acid residues may be substituted, inserted or deleted without abolishing biological or immunological activity, for instance, may be found using computer programs well known in the art, for example, DNAStar software.

The present invention relates to nucleic acid (SEQ ID NO:1 and SEQ ID NO:2) and amino acid sequences (SEQ ID NO:3) of the novel human GTPase and variations thereof and to the use of these sequences to identify compounds that modulate the activity of human GTPase and/or cell physiology.

The invention further relates to the use of the human GTPase biological switch molecule in expression systems as assays for agonists or antagonists of the biomolecule. The invention also relates to the diagnosis, study, prevention, and treatment of disease related to the human GTPase.

Polynucleotide sequences which encode the human GTPase (SEQ ID NO:3) or a functionally equivalent derivative thereof may be used in accordance with the present invention which comprise deletions, insertions and/or substitutions of the SEQ ID NO:2 nucleic acid sequence. Biologically active variants of the human GTPase molecule of the present invention may also be comprised of deletions, insertions or substitutions of SEQ ID NO:3 amino acid residues. A purified polynucleotide comprising a nucleic acid sequence encoding the polypeptide having the sequence substantially as depicted in SEQ ID NO:3 or a biologically active fragment thereof is a particularly preferred embodiment of the present invention.

Amino acid substitutions of SEQ ID NO:3 may be made, for instance, on the basis of similarity in polarity, charge, solubility, hydrophobicity, hydrophilicity, and/or the amphipathic nature of the residues as long as significant biological activity of the human GTPase is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Nucleic acid sequences which encode the amino acid sequence of the novel GTPase biological switch molecule described herein are of an exponential sum due to the potential substitution of degenerate codons (different codons which encode the same amino acid). The oligonucleotide sequence selected for heterologous expression is therefore preferably tailored to meet the most common characteristic tRNA codon recognition of the particular host expression system used as well known by those skilled in the art.

Suitable conservative substitutions of amino acids are known to those of skill in this art and may be made without altering the biological activity of the resulting polypeptide, regardless of the chosen method of synthesis. The phrase "conservative substitution" includes the use of a chemically derivatized residue in place of a non-derivatized residue provided that such polypeptide displays the desired binding activity. D-isomers as well as other known derivatives may also be substituted for the naturally occurring amino acids. See, e.g., U.S. Pat. No. 5,652,369, *Amino Acid Derivatives*, issued Jul. 29, 1997. Substitutions are preferably, although not exclusively, made in accordance with those set forth in TABLE 1 as follows:

TABLE 1

| Original residue | Conservative substitution |
|---|---|
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Pbe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

The nucleotide sequences of the present invention may also be engineered in order to alter a coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

Included within the scope of the present invention are alleles of the GTPase molecule of the present invention. As used herein, an "allele" or "allelic sequence" is an alternative form of the biological switch molecule described herein. Alleles result from nucleic acid mutations and mRNA splice-variants which produce polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The present invention relates, in part, to the inclusion of the polynucleotide encoding the novel GTPase in an expression vector which can be used to transform host cells or organisms.

Such transgenic hosts are useful for the production of the signal biomolecule and variations thereof described herein.

The nucleic acid sequence also provides for the design of antisense molecules useful in downregulating, diminishing, or eliminating expression of the genomic nucleotide sequence in cells including leukocytes, endothelial cells, and tumor or cancer cells.

The GTPase of the present invention can also be used in screening assays to identify antagonists or inhibitors which bind, emulate substrate, or otherwise inactivate or compete with the novel signal switch biomolecule. The novel GTPase can also be used in screening assays to identify agonists which enhance, activate biological activity or otherwise induce the production of or prolong the lifespan of the GTPase in vivo or in vitro.

The invention also relates to pharmaceutical compounds and compositions comprising the GTPase molecule substantially as depicted in SEQ ID NO:3, or fragments thereof, antisense molecules capable of disrupting expression of the naturally occurring gene, and agonists, antibodies, antagonists or inhibitors of the native entity biological switch. These compositions are useful for the prevention and/or treatment of conditions associated with abnormal cell physiology including but not limited to cell division, differentiation, leukocyte activity, cell activation, cell shape, motility and the like; as well as tissue physiology including but not limited to hypertension, inflammation, arteriosclerosis, angiogenesis, COPD (chronic obstructive pulmonary disease), peripheral vascular disease, diabetes, acute and chronic inflammatory disease, auto-immune disorders, rheumatoid arthritis, osteoarthritis, transplant rejection, macrophage regulation, endothelial cell regulation, fibroblasts regulation, pathological fibrosis, asthma, allergic response, ARDS, atheroma, heart failure, cancer, obeisity, cachexia, Alzheimers disease, sepsis, and neurodegeneration.

Potential diagnostic and therapeutic applications are readily apparent for modulators of the biomolecule described herein. Preferred areas which are common to disease particularly in need of therapeutic intervention include but are not limited to pathophysiological disorders manifested by dysfunctional endothelial cells, smooth muscle cells, and leukocytes.

Generally Acceptable Vectors

In accordance with the present invention, polynucleotide sequences which encode the novel GTPase, fragments of the polypeptide, fusion proteins, or functional equivalents thereof may be used in recombinant DNA molecules that direct the expression of the cellular signal biomolecule in appropriate host cells. Due to the inherent degeneracy of the genetic code, other DNA sequences which encode substantially the same or a functionally equivalent amino acid sequence, may be used to clone and express the GTPase. As will be understood by those of skill in the art, it may be advantageous to produce GTPase-encoding nucleotide sequences possessing non-naturally occurring codons.

Specific initiation signals may also be required for efficient translation of a GTPase sequence contemplated herein. These signals include the ATG initiation codon and adjacent sequences. In cases where the novel GTPase cellular switch biomolecule, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

SEQ ID NO:2, for example, may be recombinantly expressed to produce a biologically active GTPase biomolecule by molecular cloning into an expression vector containing a suitable promoter and other appropriate transcription regulatory elements, and transferred into prokaryotic or eukaryotic host cells to produce the novel polypeptide. Techniques for such manipulations are, for instance, fully described in Sambrook, J., et al., Molecular Cloning Second Edition, Cold Spring Harbor Press (1990), and are well known in the art.

Expression vectors are described herein as DNA sequences for the transcription of cloned copies of genes and the translation of their mRNAs in an appropriate host cell. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant GTPase molecule, and variations thereof contemplated herein, in mammalian cells. Commercially available mammalian expression vectors which are suitable for recombinant expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active protein. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual*, 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes a GTPase molecule of the present invention may be cultured under conditions suitable for the expression and recovery of the encoded protein from cell culture. Particularly preferred embodiments of the present invention are host cells transformed with a purified polynucleotide comprising a nucleic acid sequence encoding the polypeptide having the sequence substantially as depicted in SEQ ID NO:3 or a biologically active fragment thereof. Cells of this type or preparations made from them may be used to screen for pharmacologically active modulators of the GTPase cellular switch biomolecule activity. Modulators thus identified will be used for the regulation of biological activity and cell physiology as defined herein.

Eukaryotic recombinant host cells are especially preferred as otherwise descibed herein or are well known to those skilled in the art. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616),BS-C-1 (ATCC CCL 26) and MRC-5 (ATCC CCL 171).

The expression vector may be introduced into host cells expressing the novel GTPase via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of the switch biomolecule production. Identification of host cell clones which express the novel biomolecule may be performed by several means, including but not limited to immunological reactivity with antibodies described herein, and/or the presence of host cell-associated specific GTPase activity, and/or the ability to covalently cross-link specific substrate to the GTPase with the bifunctional cross-linking reagent disuccinimidyl suberate or similar cross-linking reagents.

The cellular signal switch biomolecule, hGTPase, of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif. 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and the GTPase is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, WI38, NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express the novel GTPase may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The human biomolecule as well as variations contemplated herein can be produced in the yeast S.cerevisiae following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, a GTPase coding region, e.g., SEQ ID NO:2, is ligated into yeast expression vectors which may employ any of a series of well-characterized secretion signals.

A variety of protocols for detecting and measuring the expression of the novel GTPase, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Methods—a Laboratory Manual*, APS Press, St Paul Minn.; Maddox, D. E., et al., J. Exp. Med. 158:1211.

Various Screening Assays

The present invention is also directed to methods for screening for compounds which modulate the biological activity of GTPase and/or cell physiology in vivo. Compounds which modulate these activities may be DNA, RNA, peptides, proteins, or non-proteinaceous organic molecules. Compounds may modulate the activity by increasing or attenuating the expression of DNA or RNA which encode the GTPase, or may antagonize or agonize the biological activity of the novel biomolecular switch itself. Compounds that modulate the expression of DNA or RNA encoding the GTPase or the function of the polypeptide may be detected by a variety of assays. The assay may be a simple "yes/no" assay to determine whether there is a change in expression or function. The assay may be made quantitative by comparing the expression or function of a test sample with the levels of expression or function in a standard sample.

The GTPase described herein, its immunoge nic fragments or oligopeptides can be used for screening therapeutic compounds in any of a variety of drug screening techniques. The fragment employed in such a test may be free in solution, affixed to a solid support, bone on a cell surface, or located intracellularly. The abolition of activity or the formnation of binding complexes, between the novel biomolecule and the agent being tested, may be measured. Accordingly, the present invention provides a method for screening a plurality of compounds for specific binding affinity with the GTPase polypeptide or a fragment thereof, comprising providing a plurality of compounds; combining the novel polypeptide of the present invention or a fragment thereof with each of a plurality of compounds for a time sufficient to allow binding under suitable conditions; and detecting binding of the trans-activator molecule, or fragment thereof, to each of the plurality of compounds, thereby identifying the compounds which specifically bind the GTPase biomolecule.

Methods of identifying compounds that modulate the activity of GTPase are generally preferred which comprise combining a candidate compound modulator of GTPase biological activity with a polypeptide GTPase having the sequenc e substantially as depicted in SEQ ID NO:3, and measuring an effect of the candidate compound modulator on the biological activity of th e GTPase (e.g., GTP binding, Calmodulin binding).

A further method of identifying compounds that modulate the biological activity of GTPase, comprises combining a candidate compound modulator of GTPase biological activity with a host-cell expressing a GTPase polypeptide having the sequence substantially as depicted in SEQ ID NO:3, and measuring an effect of the candidate compound m o dulator on the biological activity of the GTPase.

U.S. Pat. No. 5,614,370, *Assay to Identify Human C5a Antagonists and Agonists*, and methods described therein, issued Mar. 25, 1997 is herein incorporated by reference. See Examples infra.

Assay Cell Physiology

A preferred method of identifying compounds that modulate cell physiology, comprises combining a candidate compound modulator of cell physiology with a host-cell expressing a polypeptide of a human GTPase having the sequence substantially as depicted in SEQ ID NO:3, and measuring an effect of the candidate compound modulator on the cell physiology.

Methods of identifying compounds that modulate the activity of GTPase or modulate or regulate cell physiology, are also preferred which comprise combining a candidate compound modulator of GTPase with a host-cell expressing (or capable of expressing via e.g., inducible expression) the polypeptide of a GTPase molecule having the sequence substantially as depicted in SEQ ID NO:3, and measuring an effect of the candidate compound modulator on the GTPase biological activity. Preferred cellular assays for modulators fall into two general categories: 1) direct measurement of the physical GTPase biological activity, and 2) assay of cell physiology.

To measure the biological activity of the GTPase, the source may be a whole cell lysate, prepared by one to three freeze-thaw cycles in the presence of standard protease inhibitors. The GTPase may be partially or completely purified by standard protein purification methods. Preferably, the GTPase may be purified by affinity chromatography using specific antibody described herein or by ligands specific for an epitope tag engineered into the recombinant molecule moreover described herein. The preparation may then be assayed for activity.

Compounds which are identified generally according to methods descibed, referenced, and contemplated herein that modulate the activity of human GTPase (most preferably regulate physiology) are especially preferred embodiments of the present invention.

Purified polypeptides comprising the amino acid sequence substantially as depicted in SEQ ID NO:3 are especially preferred embodiments of the present invention.

A particularly preferred embodiment of the present invention is a method for treatment of a patient in need of such treatment for a condition which is mediated by human GTPase described herein comprising administration of a therapeutically effective amount of a human GTPase modulating compound.

Yeast 2-hybrid System

Because the cellular functions of GTPases are determined by their GTP-dependent affinities for binding other macromolecules including effectors as is well known in the art, a yeast 2-hybrid screen is provided to identify and characterize effectors and the like. Therefore, in another embodiment of the invention, a nuleic acid sequence which encodes a molecule substantialy as depicted in SEQ ID NO:3 or a biologically active fragment thereof may be ligated to a heterologous sequence to encode a fusion protein. For example, for screening compounds for modulation of biological activity, further described infra, it may be useful to encode a chimeric GTPase molecule as described herein for expression in hererologous host cells. Chimeric constructs may also be used to express a 'bait', according to methods well known using a yeast two-hybrid system, to identify accessory native peptides that may be associated with the novel cellular switch biomolecule described herein. Fields, S., et al., Trends Genet., 10:286 (1994); Allen, J. B., et al., TIBS, 20:511(1995). A yeast two-hybrid system has been described wherein protein:protein inte ractions can be detected using a yeast-based genetic assay via reconstitution of transcriptional activators. Fields, S., Song, O., Nature 340:245 (1989). The two-hybrid system used the ability of a pair of interacting proteins to bring a transcription activation domain into close proximity with a DNA-binding site that regulates the expression of an adjacent reporter gene. Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Stemglanz, R., TIG, 10(8):286(1994); and U.S. Pat. Nos. 5,283,173*, System to Detect Protein-Protein Interactions*, and 5,468,614, which are incorporated herein by reference.

A modified yeast two-hybrid system comprised of the GTPase described herein and Calmodulin, for example, is one example embodiment to support a high throughput (HTP) screening endeavor for such a compound. Modified screening systems, for instance, can be practiced either with a positive readout or with a negative readout such as that in the recently developed versions of "Reverse Y2H" approach. See, e.g., Vidal M, Braun P, Chen E, Boeke J D, Harlow E (1996) Genetic characterization of a mammalian protein-protein interaction domain by using a yeast reverse two-hybrid system, Proc Natl Acad Sci U S A 17;93(19):10321–10326; Vidal M, Brachmann R K, Fattacy A, Harlow E, Boeke J D (1996) Reverse two-hybrid and one-hybrid systems to detect dissociation ofprotein-protein and DNA-protein interactions. Proc Natl Acad Sci U S A 17;93(19):10315–10320; White M A (1996) The yeast two-hybrid system: forward and reverse, Proc Natl Acad Sci U S A 17;93(19):10001–10003; Leanna C A, Hannink M (1996), The reverse two-hybrid system: a genetic scheme for selection against specific protein/protein interactions, Nucleic Acids Res 1;24(17):3341–3347.

Antibodies

Monospecific antibodies to the GTPase biomolecule of the present invention are purified from mammalian antisera containing antibodies reactive against the polypeptide or are prepared as monoclonal antibodies reactive with a GTPase polypeptide using the technique of Kohler and Milstein. Nature, 256:495 (1975). Mono-specific antibody as used herein is defined as a single antibody species or multiple antibody species with homogenous binding characteristics for the novel GTPase. Homogenous binding as used herein refers to the ability of the antibody species to bind to a specific antigen or epitope, such as those associated with the novel transcription activator, as described. Human GTPase-specific antibodies are raised by immunizing animals such as mice, rats, guinea pigs, rabbits, goats, horses and the like, with rabbits being preferred, with an appropriate concentration of the GTPase either with or without an immune adjuvant.

Preimmune serum is collected prior to the first immunization. Each animal receives between about 0.1 mg and about 1000 mg of GTPase polypeptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of a GTPase polypeptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with the GTPase polypeptide are prepared by immunizing inbred mice, preferably Balb/c, with a GTPase polypeptide. The mice are immunized by the IP or SC route with about 0.1 mg to about 10 mg, preferably about 1 mg, of polypeptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of GTPase polypeptide in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using the GTPase polypeptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in *Tissue Culture Methods and Applications*, Kruse and Paterson, Eds., Academic Press (1973).

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of the anti-GTPase polypeptide mAb is carried out by growing the hydridoma in DMEM containing about 2% fetal calf serum to obtain sufficient quantities of the specific mAb. The mAb are purified by techniques known in the art.

Purification Via Affinity Columns

It is readily apparent to those skilled in the art that methods for producing antibodies may be utilized to produce antibodies specific for GTPase polypeptide fragments, or the full-length nascent human polypeptide. Specifically, it is readily apparent to those skilled in the art that antibodies may be generated which are specific for the fully functional biological signal transduction switch or fragments thereof.

Human GTPase polypeptide antibody affinity columns are made by adding the antibodies to Affigel-10(Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing GTPase polypeptide made using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. The purified polypeptide is then dialyzed against phosphate buffered saline/detergent.

Recombinant GTPase molecules can be separated from other cellular proteins by use of an immunoaffinity column made with monoclonal or polyclonal antibodies specific for full length nascent human GTPase polypeptide, or polypeptide fragments of the molecule.

GTPase polypeptides described herein may be used to affinity purify biological effectors from native biological materials, e.g. disease tissue. Affinity chromatography techniques are well known to those skilled in the art. A GTPase peptide described herein or an effective fragment thereof, is fixed to a solid matrix, e.g. CNBr activated Sepharose according to the protocol of the supplier (Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

Diagnostic Assays

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar diagnostic assays are used to detect the presence of the novel GTPase biomolecule in body fluids or tissue and cell extracts.

Diagnostic assays using GTPase polypeptide specific antibodies are useful for the diagnosis of conditions, disorders or diseases characterized by abnormal expression of the biological switch or expression of genes associated with abnormal cell growth. Diagnostic assays for the GTPase biomolecule of this invention include methods utilizing the antibody and a label to detect the human polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule, a myriad of which are well-known to those skilled in the art.

A variety of protocols for detecting and/or measuring the GTPase polypeptide, using either polyclonal or monoclonal antibodies specific for the respective protein are known in the art. Examples include enzyme-linked irnmunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the GTPase polypeptide is preferred, but a competitive binding assay may be employed. These assays are described, among other places, in Maddox, D. E. et al., J. Exp. Med. 158:1211 (1983); Sites, D. P., et al., *Basic and Clinical Immunology*, Ch.22, 4th Ed., Lange Medical Publications, Los Altos, Calif. (1982); U.S. Pat. No. 3,654,090, No. 3,850,752; and No. 4,016,043 .

In order to provide a basis for the diagnosis of disease, normal or standard values for the GTPase polypeptide expression must be established. This is accomplished by combining body fluids or cell extracts taken from normal subjects, either animal or human, with antibody to the novel signal transduction biomolecule under conditions suitable for complex formation which are well known in the art. The amount of standard complex formation may be quantified by comparing it with a dilution series of positive controls where a known amount of antibody is combined with known concentrations of purified GTPase polypeptide. Then, standard values obtained from normal samples may be compared with values obtained from samples from subjects potentially affected by a disorder or disease related to the human GTPase biomolecule expression. Deviation between standard and subject values establishes the presence of the disease state.

Kits containing GTPase nucleic acid, antibodies to a GTPase polpeptide, or protein may be prepared. Such kits are used to detect heterologous nucleic acid which hybridizes to GTPase nucleic acid, or to detect the presence of protein or peptide fragments in a sample. Such characterization is useful for a variety of purposes including, but not limited to, forensic analyses and epidemiological studies.

The DNA molecules, RNA molecules, recombinant protein and antibodies of the present invention may be used to screen and measure levels of the novel GTPase DNA, RNA or protein. The recombinant proteins, DNA molecules, RNA molecules and antibodies lend themselves to the formulation of kits suitable for the detection and typing of the human biomolecule. Such a kit will comprise a compartmentalized carrier suitable to hold in close confinement at least one container. The carrier will further comprise reagents such as recombinant human GTPase or anti-hGTPase antibodies suitable for detecting the biomolecule. The carrier may also contain a means for detection such as labeled antigen or enzyme substrates or the like.

Polynucleotide sequences which encode GTPase may be used for the diagnosis of conditions or diseases with which the expression of the novel biomolecule is associated. For example, polynucleotide sequences which encode the biomolecular switch may be used in hybridization or PCR assays of fluids or tissues from biopsies to detect expression of the GTPase. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regime in animal studies, in clinical trials, or in monitoring the treatment of an individual patient. Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polynucleotide sequences which encode the signal transduction biomolecule may also be employed in analyses to map chromosomal locations, e.g., screening for functional association with disease markers. Moreover the sequences described herein are contemplated for use to identify human sequence polymorphisms and possible association with disease as well as analyses to select optimal sequence from among possible polymorphic sequences for the design of compounds to modulate GTPase biological activity and therefore regulate cell physiology, most preferably in vivo. Furthermore the sequences are contemplated as screening tools for use in the identification of appropriate human subjects and patients for therapeutic clinical trials.

PCR Diagnostics

The nucleic acid sequence, oligonucleotides, fragments, portions or antisense molecules thereof, may be used in diagnostic assays of body fluids or biopsied tissues to detect the expression level of the GTPase molecule. For example, sequences designed from the cDNA sequence SEQ ID NO:1 or sequences comprised in SEQ ID NO:2 can be used to detect the presence of the mRNA transcripts in a patient or to monitor the modulation of transcripts during treatment.

One method for amplification of target nucleic acids, or for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. One example embodiment of the present invention is a diagnostic composition for the identification of a polynucleotide sequence comprising the sequence substantially as depicted in SEQ ID NO:2 comprising the PCR primers substantially as depicted in Example II. The degree of amplification of a target sequence is controlled by the number of cycles that are performed and is theoretically calculated by the simple formula 2n where n is the number of cycles. See, e.g., Perkin Elmer, *PCR Bibliography,* Roche Molecular Systems, Branchburg, N.J.; CLONTECH products, Palo Alto, Calif.; U.S. Pat. No. 5,629,158*, Solid Phase Diagnosis of Medical Conditions,* issued May 13, 1997.

Antisense Molecules

Previously characterized Ras-like genes including the Rad, Gem, and Kir genes are known to be regulated by transcriptional induction. The cDNA sequence SEQ ID NO:1 provided herein, may be used in another embodiment of the invention to regulate expression of the novel human GTPase in cells by the use of anti-sense constructs.

To enable methods of down-regulating expression of the hGTPase of the present invention in mammalian cells, an example antisense expression construct containing the complement DNA sequence to the sequence substantially as depicted in SEQ ID NO:2 can be readily constructed for instance using the pREP10 vector (Invitrogen Corporation). Transcripts are expected to inhibit translation of the wild-type GTPase mRNA in cells transfected with this type construct. Antisense transcripts are effective for inhibiting translation of the native gene transcript, and capable of inducing the effects (e.g., regulation of tissue physiology) herein described. Translation is most effectively inhibited by blocking the mRNA at a site at or near the initiation codon. Thus, oligonucleotides complementary to the corresponding 5'-terminal region of the human GTPase mRNA transcript are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome appears to unravel the antisense/sense duplex to permit translation of the message. Oligonucleotides which are complementary to and hybridizable with any portion of the novel human GTPase mRNA are contemplated for therapeutic use.

U.S. Pat. No. 5,639,595, *Identification of Novel Drugs and Reagents,* issued Jun. 17, 1997, wherein methods of identifying oligonucleotide sequences that display in vivo activity are thoroughly described, is herein incorporated by reference. Expression vectors containing random oligonucleotide sequences derived from previously known polynucleotides are transformed into cells. The cells are then assayed for a phenotype resulting from the desired activity of the oligonucleotide. Once cells with the desired phenotype have been identified, the sequence of the oligonucleotide having the desired activity can be identified.

Identification may be accomplished by recovering the vector or by polymerase chain reaction (PCR) amplification and sequencing the region containing the inserted nucleic acid material.

Nucleotide sequences that are complementary to the GTPase polypeptide encoding polynucleotide sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, *Hybrid Oligonucleotide Phosphorothioates,* issued Jul. 29, 1997, and U.S. Pat. No. 5,652,356, *Inverted Chimeric and Hybrid Oligonucleotides,* issued Jul. 29, 1997, which describe the synthesis and effect of physiologically-stable antisense molecules, are incorporated by reference. GTPase antisense molecules may be introduced into cells by microinjection, liposome encapsulation or by expression from vectors harboring the antisense sequence. Antisense therapy may be particularly useful for the treatment of diseases where it is beneficial to modulate cell physiology.

Gene Therapy

GTPase described herein may administered to a subject via gene therapy. A polypeptide of the present invention may be delivered to the cells of target organs in this manner. Conversely, hGTPase polypeptide antisense gene therapy may be used to modulate the expression of the polypeptide in the cells of target organs and hence regulate cell physiology. The human GTPase polypeptide coding region can be ligated into viral vectors which mediate transfer of the trans-activator polypeptide nucleic acid by infection of recipient host cells. Suitable viral vectors include retrovirus, adenovirus, adeno-associated virus, herpes virus, vaccinia virus, polio virus and the like. See, e.g., U.S. Pat. No. 5,624,820, *Episomal Expression Vector for Human Gene Therapy,* issued Apr. 29, 1997.

Nucleic acid coding regions of the present invention are incorporated into effective eukaryotic expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, GTPase polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo gene therapy according to established methods in this art.

Compositions

Pharmaceutically useful compositions comprising sequences pertaining to the novel human GTPase polypeptide DNA, RNA, antisense sequences, or the human switch biomolecule itself, or variants and analogs which have the human GTPase biological activity or otherwise modulate cellular physiology, may be formulated according to known methods such as by the admixture of a pharmaceutically acceptable carrier. Examples of such carriers and methods of formulation may be found in *Remington's Pharmaceutical Sciences* (Maack Publishing Co, Easton, Pa.). To form a pharmaceutically acceptable composition suitable for effective administration, such compositions will contain an effective amount of the protein, DNA, RNA, or compound modulator.

Therapeutic or diagnostic compositions of the invention are administered to an individual in amounts sufficient to treat or diagnose GTPase related disorders. The effective amount may vary according to a variety of factors such as the individual's condition, weight, sex and age. Other factors include the mode of administration.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences.*

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of protein or its antibodies, antagonists, or inhibitors which ameliorate the symptoms or condition. The exact dosage is chosen by the individual physician in view of the patient to be treated.

Compounds identified according to the methods disclosed herein may be used alone at appropriate dosages defined by routine testing in order to obtain optimal modulation of hGTPase biological activity or its effect on cell or tissue physiology while minimizing any potential toxicity. In addition, co-administration or sequential administration of other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of hGTPase can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a GTPase modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the GTPase modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

Identification

A region of the novel C-terminus (RSKSCHNLAVL) was used to probe a proprietary database. One related EST (containing the code for the related peptide sequence KSKSCHDLSVL) was identified. Northern blot analysis (CLONTECH blot) showed that the sequence was expressed in human lymph node and spleen. Sequences of this EST were then used to screen a phage λ human lymph node cDNA library (CLONTECH library). Three full length clones, containing the coding region and flanking region were identified and sequenced.

Example II

Construction of GST Fusion Construct:

The coding region of of the novel biomolecule described herein was PCR amplified from human lymph node library phage DNA (CLONTECH), oligos: 5' ATGGATCCACACTCAACACCGAGCAGG 3' and 5' TCTCGAGTCAGAGCACGGCCAGATTG 3' were used as primers. The PCR product was digested with BamH I and Xho I, and ligated into BamH I and Xho I digested vector pGEX-6P-1 (Pharmacia Biotech, Cat #27-4597-01).

Example III

Expression and Purification of GST Fusion Protein pGEX-6P-1 containing the novel coding sequence was introduced into BL21 cells by standard transformation. A single positive colony was inoculated into 2xYT medium containing 50 μg/ml carbenicillin and grown at 37° C. until $OD_{600}$ reached 0.5. IPTG was added to 0.2 mM to induce protein expression at room temperature for 3 hours. Cells were spun down and resuspend in 1/10 the volume of PBS (1.4M NaCl, 27 mM KCl, 101 mM $Na_2HPO_4$), 18 mM $KH_2PO_4$, pH 7.3). Lysozyme was added to 100 μg/ml and incubated on ice for 30 minutes. CHAPs was added (3-[(3-Cholamidopropyl)dimethyl-ammoniol]-1-propanesulfonate) to reach 1% as protease inhibitors. The mixture was sonicated for 1 minute and centrifuged 10 min. at 14,000×g. Glutathione Sepharose 4B beads (Pharmacia, Cat #:17-0756-01) were washed with PBS and packed into a standard column. The clear supernatant was passed from the cell lysate via standard procedure through the column. The column was washed with 10 bed volumes of PBS. The active fusion protein was eluted from the column with 50 mM Tris-HCl, pH8.0, 10 mM Glutathione.

Example IV

GTP Binding Assay

The purified fusion protein was electrophoresed on a 12% polyacrylamide gel. The protein was transferred from the gel onto a standard nitrocellulose membrane. The membrane was subsequently incubated in binding buffer (50 mM Tris-HCl, pH7.5, 5 mM $MgCl_2$,2 mM DTT, 0.3% Tween-20, 0.3% BSA, 0.1 mM ATP) at room temperature for 1 hour. The membrane was subsequently transferred into 25 ml fresh binding buffer containing 3 μl $^{32}$P GTP (NEN, Cat #: Blu-006x) and incubated at room temperature for 1 hour. The membrane was washed with fresh binding buffer for 5 minutes three times. The membrane is blotted dry, and wrapped with plastic (Saran) wrap and exposed to X-ray film overnight. The active protein binds to $^{32}$P-GTP which is clearly indicated by an autoradiographed band on the film.

Example V

Calmodulin Binding Assay

A nucleic acid sequence which encodes the novel GTPase, e.g., SEQ ID NO:1, can be ligated into any vector that contains a T7 promoter, for instance, such as TOPO TA cloning vector (Invitrogen, Cat #: K400-01). The protein is synthesized in vitro in TNT T7 coupled reticulocyte lysate system (Promega, Cat #:L4610) in the presence of L-[35S]-

Cysteine (NEN, Cat #: NEG-022T). Add lmM Calcium into the lysate containing radio-labeled GTPase of the present invention and pass it through a Calmodulin Sepharose 4B column. The column is washed with PBS containing 1 mM $Ca^{2+}$, and eluted with PBS containing 2 mM EGTA. The eluent is electrophoresed on a 12% polyacrylamide gel. The gel is dried and exposed to X-ray film at −70° C. overnight. The radiolabeled novel GTPase that was eluted from the calmodulin column is clearly indicated by an autoradiographed band on the film.

Example VI

High Throughput Screening for Compounds Which Modulate GTPase Activity

High throughput screening for modulator compounds is performed using MBP coated 96-well FlashPlates® (NEN™ Life Science Products). Reaction buffer (3× reaction buffer (KRB) contains: 60 mM HEPES (pH 7.5), 30 mM magnesium acetate, 0.15 mM ATP, 3 mM DTT, 0.03 mM sodium orthovanadate) 0.25 μCi [$\gamma^{33}$P]-GTP at a concentration no greater than 1 μg/ml, (determined by titration of individual enzyme preparations for a concentration that allows kinetic determinations over a 1 hour time course of the human GTPase) are added to each well and incubated 1 hour at 30° C. in the presence or absence of 10 μM test compound. Total reaction volume is 100 μL. Following incubation, the reaction mixture is aspirated and the wells rinsed 2 times with 300 μL PBS. Incorporation of raiolabeled phosphate is determined by scintillation counting, Packard Instrument Co.TopCount, 12-detector, 96-well microplate scintillation counter and luminescence counter, model B991200. Compounds which inhibit GTPase activity ≧50 percent at 10 μM are are indicated by a >50% reduction in scintillation counts. Specificity and selectivity studies is determined by titration of inhibitory compounds to determine the $IC_{50}$ (or other standard quantitation well known in the art for comparison) and by the substitution of other GTPases in the assay. For example, determination of relative inhibitory activity of the kinase in comparison to recombinant Rem, Gem or Rad expressed and isolated in a similar manner, assayed under similar conditions, provides selectivity data.

Example VII

High Throughput Screening Protocol

Test Compounds Test compounds are prepared in advance from 2.5 mg/ml stock solutions in DMSO by diluting 1:10 in distilled water and then 1:10 again. Ten (10 μl of the 1:100 dilution solutions (25 μg/ml in 1% DMSO) are prepared in 96 well Microlite 1 plates (Dynatech) and plates are stored at −20° C. until the evening prior to the start of the assay.

Control plates A plate containing control solutions is included in each run of the screen for QA purposes. Such plates are prepared at the beginning of the HTS campaign and stored at −20° C. until required. Zero inhibition (MAX. signal) wells (columns 3, 6, 8 and 10) contain 10 μl of 1% (v/v) DMSO solution in MilliQ water. 100% inhibition (MIN signal) wells (columns 1, 4, 9 and 11) contain 10 μl of 220 nM ZM333141/1 in 1% DMSO solution in MilliQ water. 50% inhibition (REF. signal) wells (columns 2, 5, 7 and 12) contain a reference compound at a concentration known to provide approximately 50% inhibition in 1% (v/v) DMSO solution in MilliQ water.

Assay Components (1) recombinant GTPase (expressed in *E. coli* or eukaryotic cells as described herein) or a lysate of a prokaryotic or eukaryotic cell expressing recombinant enzyme, or the natural enzyme partially purified from a human cell line.

(2) [$\gamma^{33}$-P]-GTP (3) The GST fusion protein is immobilized on "scintillation proximity" beads that are linked to glutathione (the GST will bind to the SPA beads). A scintillation proximity assay is carried out, using 33P-labeled GTP as a ligand.

To Microlite I plates containing 10 μl of test compound, which have been left on the bench overnight to reach room temperature, 25 ml of GST-Rb/GTP/$GTP^{33}$ is added, immediately followed by 20 μl of Enzyme, using two Multidrops. The plates are stacked in 13 plate stacks (with an empty plate on top of each stack to minirise evaporation from the top plate) and left at room temperature for 105 minutes. 150 μl of "Stop Solution" containing beads antibody and EDTA is added using a Multidrop. The plates are sealed with Topseal-S plate sealers and left on the bench overnight, surrounded by Scotlab perspex screens. The plates are then centrifuged (Heraeus Megafuge 3.0R) at 2500 rpm, 1124xg., for 5 minutes (2 plates per trunnion) and counted on a Topcount (I4.34); (isotope:$P^{33}$; counting time: 20 seconds/well).

The data may be analys ed using w ell-known s oftwa re systems. A threshold for inhibition is set, e.g., 60% inhibition of scintillation signal. Compounds reaching the inhibition threshold are scored as active.

EXAMPLE VIII

GTPase Activity Assay

The method of Kupper et al. (Kupper, R. W., Dewald, B., Jakobs, K. H., Baggiolini, M. and Gierschik, P. (1992) Biochem. J. 282, 429–434) is adapted for use in microtiter plates. Neutrophil membranes are suspended in 50 mM triethanolamine-HCl, 5 MM MES, pH 7.3, containing 1 mM EDTA, 5 mM $MgCl_2$, 143 mM NaCl, 0.16% BSA, 1 mM ouabain, 1 mM AMP-PNP, 0.5 mM ATP, 2.5 U/mL creatine phosphokinase, 10 mM creatine phosphate, 0.1 mM PMSF and 10 ng/mL each of leupeptin, aprotinin and chymostatin. 50 mu L of membranes containing 1–5 mu g protein are added to 50 mu L of the same buffer containing the test agent and 0.25 mu M [gamma-$^{32}$P]-GTP (2,000 cpm/pmol) in the wells of a U-shaped microtiter plate. After incubation for 15–30 rain at 29° C., 100 mu L of a 10% (w/v) charcoal suspension in 100 mM $H_3PO_4$ is added and plates are centrifuged at 2000 rpm for 5 min. 100 mu L of the supernatant is transferred to an Optiplate microtiter plate and 100 mu L of Microscint-40 scintillation cocktail is added. Control and sample wells are counted in a Packard TopCount microtiter plate counter. Similar results have been obtained in experiments which monitor ligand stimulated increases in GTP gamma S binding. See, U.S. Pat. No. 5,614,370, issued Mar. 25, 1997.

EXAMPLE VIII

Immunoprecipitation

Immunoprecipitation of the human GTPase molecule described herein is performied substantially according to the method described by Suchard, S.J., et al. J. Immunol., 158:4961 (1997). Cell lysates are combined with 1 μg of peptide-specific monoclonal or polyclonal an tibody against the native GTPase described herein. Rabbit IgG is used as a control. Samples are incubated at 4° C.≧2 hours with rotation. Immunocomplexes are incubated with protein A Sepharose (Pharmacia) for 2 hours at 4° C. with rotation. The beads are washed in buffer containing 50 mM Tris (pH 8.0), 100 mM NaCl, 1 mM $Na_3VO_4$, 1% Triton X-100, and Complete™ Protease Inhibitor Cocktail. Adsorbed proteins are solubilized in sample buffer and separated on 12% SDS-PAGE minigels.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polynucleotide comprising a nucleic acid sequence encoding the polypeptide having the sequence as depicted in SEQ ID NO:3 or a variant of SEQ ID NO:3 that differs from SEQ ID NO:3 by one or more conservative amino acid substitutions.

2. The polynucleotide of claim 1 wherein the polynucleotide sequence comprises the sequence as depicted in SEQ ID NO:2.

3. An expression vector comprising the polynucleotide of claim 1.

4. An antisense molecule comprising the complement of the polynucleotide of claim 2.

5. A host cell transformed with the expression vector of claim 3.

6. A method for producing cells which express a biologically active polypeptide as depicted in SEQ ID NO:3 or a variant of SEQ ID NO:3 that differs from SEQ ID NO:3 by one or more conservative amino acid substitutions, said method comprising a) culturing a host cell according to claim 5 under conditions suitable for the expression of said polypeptide.

7. A method for producing a polypeptide having the amino acid sequence as depicted in SEQ ID NO:3 or a variant of SEQ ID NO:3 that differs from SEQ ID NO:3 by one or more conservative amino acid substitutions, said method comprising the steps of:

a) culturing a host cell according to claim 5 under conditions suitable for the expression of said polypeptide, and b) recovering said polypeptide from the host cell culture.

* * * * *

SEQUENCE LISTING

<160> NUMBER OF SEQ ID NOS: 7

<210> SEQ ID NO 1
<211> LENGTH: 1525
<212> TYPE: DNA
<213> ORGANISM: Homo sapiens

<400> SEQUENCE: 1

```
cacagcctgg agcatccagc cgctggagct gcgagggacc ctggacccct cccacgccga     60

ggtttatgca gagcctgagg ccagaaaacc tagggacttt ctgccccaag aagctgaggc    120

acctcctact cccatctgaa caagaggggg atctggaaga agccatacag cagctcatca    180

ggacactata gaaagaagca gctcaaagca attggctgac agccaattcc cccttctttc    240

agaaggaaag aaggaagaag caaacccccc cctaccaaag atgacactca acaccgagca    300

ggaagcaaag acccctctgc accggcgagc cagcacccca ctgcccctgt ccccacgggg    360

ccaccagcct ggccgcctga gcacagtgcc ttccactcaa tcccagcatc cccggctggg    420

ccaatcagcc tccctcaacc ctcccaccca gaaaccttca cctgccccag atgattggtc    480

ttctgaatcc agcgactctg aaggctcctg ggaggctctc taccgtgtgg tgctacttgg    540

agatcctgga gtggggaaga ccagcttggc cagcctcttt gcagggaagc aagagaggga    600

cctccatgaa cagctgggag aagatgtata tgagaggacc ctcacggtgg atggagaaga    660

caccacactg gtggtcgtgg acacctggga ggccgagaaa ctggataaaa gctggagcca    720

ggagtcatgc ctgcaggggg gcagtgccta tgtcatcgta tactccatcg cagaccgagg    780

cagctttgag agtgcctctg agctccgcat ccagctgcgg cgcacacatc aggcagacca    840

tgtgcccatc atcctcgtgg gcaacaaggc agacttggcc cgctgccgag aagtctctgt    900

ggaagagggc cgcgcctgcg ctgtggtgtt cgactgtaaa ttcatcgaga catccgccac    960

gctgcagcac aatgtggccg agctcttcga gggcgtggtg cgccaactgc gcttgcgccg   1020

ccgggacagt gcggccaagg aacccccagc accccgacgg ccggccagcc tagcccagcg   1080

cgctcgtcgc ttcctggcac gcctgacagc ccgcagcgca cgccgccggg cactcaaggc   1140

ccgctccaag tcctgccaca atctggccgt gctctgaagc cccccgccct tctgagagtt   1200

ggcgggtcac tgaggtgcat tctgggctcc agggacgcca ctgcggggca aaggcgccgt   1260

tacctggagt ctgcatcatg ggtcttgctt gcctgctgcc ctgatggcct gagcatcccc   1320

cagatccaag cctgggggat cccgggaaag cgatggacag acagacgatg gggccgaagc   1380

cccaagctgg gcacaaagta gttttttacg tggtgggtgt ctttttgtaa aaaaatcttc   1440

cttgtccctg ggctctggcc aaccctcaga aaccctcaca ataaaccaga ccagaaggat   1500

gtcccaaaaa aaaaaaaaaa aaaaa                                         1525
```

<210> SEQ ID NO 2
<211> LENGTH: 897
<212> TYPE: DNA
<213> ORGANISM: Homo sapiens

<400> SEQUENCE: 2

-continued

```
atgacactca acaccgagca ggaagcaaag acccctctgc accggcgagc cagcacccca     60

ctgcccctgt ccccacgggg ccaccagcct ggccgcctga gcacagtgcc ttccactcaa    120

tcccagcatc cccggctggg ccaatcagcc tccctcaacc ctcccaccca gaaaccttca    180

cctgccccag atgattggtc ttctgaatcc agcgactctg aaggctcctg ggaggctctc    240

taccgtgtgg tgctacttgg agatcctgga gtggggaaga ccagcttggc cagcctcttt    300

gcagggaagc aagagaggga cctccatgaa cagctgggag aagatgtata tgagaggacc    360

ctcacggtgg atggagaaga caccacactg gtggtcgtgg acacctggga ggccgagaaa    420

ctggataaaa gctggagcca ggagtcatgc ctgcaggggg gcagtgccta tgtcatcgta    480

tactccatcg cagaccgagg cagctttgag agtgcctctg agctccgcat ccagctgcgg    540

cgcacacatc aggcagacca tgtgcccatc atcctcgtgg gcaacaaggc agacttggcc    600

cgctgccgag aagtctctgt ggaagagggc cgcgcctgcg ctgtggtgtt cgactgtaaa    660

ttcatcgaga catccgccac gctgcagcac aatgtggccg agctcttcga gggcgtggtg    720

cgccaactgc gcttgcgccg ccgggacagt gcggccaagg aacccccagc accccgacgg    780

ccggccagcc tagcccagcg cgctcgtcgc ttcctggcac gcctgacagc ccgcagcgca    840

cgccgccggg cactcaaggc ccgctccaag tcctgccaca atctggccgt gctctga       897
```

<210> SEQ ID NO 3
<211> LENGTH: 298
<212> TYPE: PRT
<213> ORGANISM: Homo sapiens

<400> SEQUENCE: 3

```
Met Thr Leu Asn Thr Glu Gln Glu Ala Lys Thr Pro Leu His Arg Arg
 1               5                  10                  15

Ala Ser Thr Pro Leu Pro Leu Ser Pro Arg Gly His Gln Pro Gly Arg
            20                  25                  30

Leu Ser Thr Val Pro Ser Thr Gln Ser Gln His Pro Arg Leu Gly Gln
        35                  40                  45

Ser Ala Ser Leu Asn Pro Pro Thr Gln Lys Pro Ser Pro Ala Pro Asp
    50                  55                  60

Asp Trp Ser Ser Glu Ser Ser Asp Ser Glu Gly Ser Trp Glu Ala Leu
65                  70                  75                  80

Tyr Arg Val Val Leu Leu Gly Asp Pro Gly Val Gly Lys Thr Ser Leu
                85                  90                  95

Ala Ser Leu Phe Ala Gly Lys Gln Glu Arg Asp Leu His Glu Gln Leu
            100                 105                 110

Gly Glu Asp Val Tyr Glu Arg Thr Leu Thr Val Asp Gly Glu Asp Thr
        115                 120                 125

Thr Leu Val Val Val Asp Thr Trp Glu Ala Glu Lys Leu Asp Lys Ser
    130                 135                 140

Trp Ser Gln Glu Ser Cys Leu Gln Gly Gly Ser Ala Tyr Val Ile Val
145                 150                 155                 160

Tyr Ser Ile Ala Asp Arg Gly Ser Phe Glu Ser Ala Ser Glu Leu Arg
                165                 170                 175

Ile Gln Leu Arg Arg Thr His Gln Ala Asp His Val Pro Ile Ile Leu
            180                 185                 190

Val Gly Asn Lys Ala Asp Leu Ala Arg Cys Arg Glu Val Ser Val Glu
        195                 200                 205

Glu Gly Arg Ala Cys Ala Val Val Phe Asp Cys Lys Phe Ile Glu Thr
    210                 215                 220
```

```
Ser Ala Thr Leu Gln His Asn Val Ala Glu Leu Phe Glu Gly Val Val
225                 230                 235                 240

Arg Gln Leu Arg Leu Arg Arg Arg Asp Ser Ala Ala Lys Glu Pro Pro
                245                 250                 255

Ala Pro Arg Arg Pro Ala Ser Leu Ala Gln Arg Ala Arg Arg Phe Leu
            260                 265                 270

Ala Arg Leu Thr Ala Arg Ser Ala Arg Arg Arg Ala Leu Lys Ala Arg
        275                 280                 285

Ser Lys Ser Cys His Asn Leu Ala Val Leu
    290                 295


<210> SEQ ID NO 4
<211> LENGTH: 297
<212> TYPE: PRT
<213> ORGANISM: Mus musculus

<400> SEQUENCE: 4

Met Thr Leu Asn Thr Gln Gln Glu Ala Lys Thr Thr Leu Arg Arg Arg
 1               5                  10                  15

Ala Ser Thr Pro Leu Pro Leu Ser Ser Arg Gly His Gln Pro Gly Arg
            20                  25                  30

Leu Cys Thr Ala Pro Ser Ala Pro Ser Gln His Pro Arg Leu Gly Gln
        35                  40                  45

Ser Val Ser Leu Asn Pro Pro Val Arg Lys Pro Ser Pro Ala Gln Asp
    50                  55                  60

Gly Trp Ser Ser Glu Ser Ser Asp Ser Glu Gly Ser Trp Glu Ala Leu
65                  70                  75                  80

Tyr Arg Val Val Leu Leu Gly Asp Pro Gly Val Gly Lys Thr Ser Leu
                85                  90                  95

Ala Ser Leu Phe Ala Glu Lys Gln Asp Arg Asp Pro His Glu Gln Leu
            100                 105                 110

Gly Gly Val Tyr Glu Arg Thr Leu Ser Val Asp Gly Glu Asp Thr Thr
        115                 120                 125

Leu Val Val Met Asp Thr Trp Glu Ala Glu Lys Leu Asp Glu Ser Trp
    130                 135                 140

Cys Gln Glu Ser Cys Leu Gln Ala Gly Ser Ala Tyr Val Ile Val Tyr
145                 150                 155                 160

Ser Ile Ala Asp Arg Ser Ser Phe Glu Ser Ala Ser Glu Leu Arg Ile
                165                 170                 175

Gln Leu Arg Arg Thr His Gln Ala Asn His Val Pro Ile Ile Leu Val
            180                 185                 190

Gly Asn Lys Ala Asp Leu Ala Arg Cys Arg Glu Val Ser Val Glu Glu
        195                 200                 205

Gly Arg Ala Cys Ala Val Val Phe Asp Cys Lys Phe Ile Glu Thr Ser
    210                 215                 220

Ala Thr Leu Gln His Asn Val Thr Glu Leu Phe Glu Gly Val Val Arg
225                 230                 235                 240

Gln Leu Arg Leu Arg Arg Gln Asp Asn Ala Ala Pro Glu Thr Pro Ser
                245                 250                 255

Pro Arg Arg Arg Ala Ser Leu Gly Gln Arg Ala Arg Arg Phe Leu Ala
            260                 265                 270

Arg Leu Thr Ala Arg Ser Ala Arg Arg Arg Ala Leu Lys Ala Arg Ser
        275                 280                 285

Lys Ser Cys His Asn Leu Ala Val Leu
    290                 295
```

<210> SEQ ID NO 5
<211> LENGTH: 296
<212> TYPE: PRT
<213> ORGANISM: Homo sapiens

<400> SEQUENCE: 5

```
Met Thr Leu Asn Asn Val Thr Met Arg Gln Gly Thr Val Gly Met Gln
 1               5                  10                  15

Pro Gln Gln Gln Arg Trp Ser Ile Pro Ala Asp Gly Arg His Leu Met
            20                  25                  30

Val Gln Lys Glu Pro His Gln Tyr Ser His Arg Asn Arg His Ser Ala
        35                  40                  45

Thr Pro Glu Asp His Cys Arg Arg Ser Trp Ser Ser Asp Ser Thr Asp
    50                  55                  60

Ser Val Ile Ser Ser Glu Ser Gly Asn Thr Tyr Tyr Arg Val Val Leu
65                  70                  75                  80

Ile Gly Glu Gln Gly Val Gly Lys Ser Thr Leu Ala Asn Ile Phe Ala
                85                  90                  95

Gly Val His Asp Ser Met Asp Ser Asp Cys Glu Val Leu Gly Glu Asp
            100                 105                 110

Thr Tyr Glu Arg Thr Leu Met Val Asp Gly Glu Ser Ala Thr Ile Ile
        115                 120                 125

Leu Leu Asp Met Trp Glu Asn Lys Gly Glu Asn Glu Trp Leu His Asp
    130                 135                 140

His Cys Met Gln Val Gly Asp Ala Tyr Leu Ile Val Tyr Ser Ile Thr
145                 150                 155                 160

Asp Arg Ala Ser Phe Glu Lys Ala Ser Glu Leu Arg Ile Gln Leu Arg
                165                 170                 175

Arg Ala Arg Gln Thr Glu Asp Ile Pro Ile Ile Leu Val Gly Asn Lys
            180                 185                 190

Ser Asp Leu Val Arg Cys Arg Glu Val Ser Val Ser Glu Gly Arg Ala
        195                 200                 205

Cys Ala Val Val Phe Asp Cys Lys Phe Ile Glu Thr Ser Ala Ala Val
    210                 215                 220

Gln His Asn Val Lys Glu Leu Phe Glu Gly Ile Val Arg Gln Val Arg
225                 230                 235                 240

Leu Arg Arg Asp Ser Lys Glu Lys Asn Glu Arg Arg Leu Ala Tyr Gln
                245                 250                 255

Lys Arg Lys Glu Ser Met Pro Arg Lys Ala Arg Arg Phe Trp Gly Lys
            260                 265                 270

Ile Val Ala Lys Asn Asn Lys Asn Met Ala Phe Lys Leu Lys Ser Lys
        275                 280                 285

Ser Cys His Asp Leu Ser Val Leu
    290                 295
```

<210> SEQ ID NO 6
<211> LENGTH: 269
<212> TYPE: PRT
<213> ORGANISM: Homo sapiens

<400> SEQUENCE: 6

```
Met Pro Val Asp Glu Arg Asp Leu Gln Ala Ala Leu Thr Pro Gly Ala
 1               5                  10                  15

Leu Thr Ala Ala Ala Ala Gly Thr Gly Thr Gln Gly Pro Arg Leu Asp
            20                  25                  30

Trp Pro Glu Asp Ser Glu Asp Ser Leu Ser Ser Gly Gly Ser Asp Ser
```

-continued

```
        35                  40                  45

Asp Glu Ser Val Tyr Lys Val Leu Leu Leu Gly Ala Pro Gly Val Gly
    50                  55                  60

Lys Ser Ala Leu Ala Arg Ile Phe Gly Gly Val Glu Asp Gly Pro Glu
65                  70                  75                  80

Ala Glu Ala Ala Gly His Thr Tyr Asp Arg Ser Ile Val Val Asp Gly
                85                  90                  95

Glu Glu Ala Ser Leu Met Val Tyr Asp Ile Trp Glu Gln Asp Gly Gly
            100                 105                 110

Arg Trp Leu Pro Gly His Cys Met Ala Met Gly Asp Ala Tyr Val Ile
        115                 120                 125

Val Tyr Ser Val Thr Asp Lys Gly Ser Phe Glu Lys Ala Ser Glu Leu
    130                 135                 140

Arg Val Gln Leu Arg Arg Ala Arg Gln Thr Asp Asp Val Pro Ile Ile
145                 150                 155                 160

Leu Val Gly Asn Lys Ser Asp Leu Val Arg Ser Arg Glu Val Ser Val
                165                 170                 175

Asp Glu Gly Arg Ala Cys Ala Val Val Phe Asp Cys Lys Phe Ile Glu
            180                 185                 190

Thr Ser Ala Ala Leu His His Asn Val Gln Ala Leu Phe Glu Gly Val
        195                 200                 205

Val Arg Gln Ile Arg Leu Arg Arg Asp Ser Lys Glu Ala Asn Ala Arg
    210                 215                 220

Arg Gln Ala Gly Thr Arg Arg Arg Glu Ser Leu Gly Lys Lys Ala Lys
225                 230                 235                 240

Arg Phe Leu Gly Arg Ile Val Ala Arg Asn Ser Arg Lys Met Ala Phe
                245                 250                 255

Arg Ala Lys Ser Lys Ser Cys His Asp Leu Ser Val Leu
            260                 265


<210> SEQ ID NO 7
<211> LENGTH: 897
<212> TYPE: DNA
<213> ORGANISM: Artificial Sequence
<220> FEATURE:
<223> OTHER INFORMATION: Example Dominant Negative GTPase Structural
      Coding Region

<400> SEQUENCE: 7

atgacactca acaccgagca ggaagcaaag acccctctgc accggcgagc cagcacccca      60

ctgcccctgt ccccacgggg ccaccagcct ggccgcctga gcacagtgcc ttccactcaa     120

tcccagcatc cccggctggg ccaatcagcc tccctcaacc ctcccaccca gaaaccttca     180

cctgccccag atgattggtc ttctgaatcc agcgactctg aaggctcctg ggaggctctc     240

taccgtgtgg tgctacttgg agatcctgga gtggggaaga acagcttggc cagcctcttt     300

gcagggaagc aagagaggga cctccatgaa cagctgggag aagatgtata tgagaggacc     360

ctcacggtgg atggagaaga caccacactg gtggtcgtgg acacctggga ggccgagaaa     420

ctggataaaa gctggagcca ggagtcatgc ctgcaggggg gcagtgccta tgtcatcgta     480

tactccatcg cagaccgagg cagctttgag agtgcctctg agctccgcat ccagctgcgg     540

cgcacacatc aggcagacca tgtgcccatc atcctcgtgg gcaacaaggc agacttggcc     600

cgctgccgag aagtctctgt ggaagagggc cgcgcctgcg ctgtggtgtt cgactgtaaa     660

ttcatcgaga catccgccac gctgcagcac aatgtggccg agctcttcga gggcgtggtg     720

cgccaactgc gcttgcgccg ccgggacagt gcggccaagg aacccccagc accccgacgg     780
```

-continued

```
ccggccagcc tagcccagcg cgctcgtcgc ttcctggcac gcctgacagc ccgcagcgca    840

cgccgccggg cactcaaggc ccgctccaag tcctgccaca atctggccgt gctctga       897
```